US012213993B2

(12) United States Patent
McCord et al.

(10) Patent No.: US 12,213,993 B2
(45) Date of Patent: Feb. 4, 2025

(54) COATED MEDICINAL CLAY COMPOSITIONS, PHARMACEUTICAL COMPOSITIONS, AND DELIVERY OF CATION SOURCES AND METHODS OF USE THEREOF

(71) Applicant: Darlene E. McCord, Chattanooga, TN (US)

(72) Inventors: Darlene E. McCord, Chattanooga, TN (US); Alex Hovey, North Liberty, IA (US)

(73) Assignee: Darlene E. McCord, Chattanooga, TN (US)

( * ) Notice: Subject to any disclaimer, the term of this patent is extended or adjusted under 35 U.S.C. 154(b) by 0 days.

(21) Appl. No.: 18/049,095

(22) Filed: Oct. 24, 2022

(65) Prior Publication Data
US 2023/0131873 A1    Apr. 27, 2023

Related U.S. Application Data

(60) Provisional application No. 63/364,657, filed on May 13, 2022, provisional application No. 63/262,999, filed on Oct. 25, 2021.

(51) Int. Cl.
*A61K 33/26* (2006.01)
*A61K 33/06* (2006.01)
(Continued)

(52) U.S. Cl.
CPC ............. *A61K 33/26* (2013.01); *A61K 33/06* (2013.01); *A61K 33/38* (2013.01); *A61P 31/04* (2018.01)

(58) Field of Classification Search
CPC ........ A61K 33/06; A61K 33/38; A61K 33/24; A61K 33/30; A61K 33/34; A61P 31/04
(Continued)

(56) References Cited

U.S. PATENT DOCUMENTS 3,449,492 A    6/1969  Jensen
4,946,829 A    8/1990  Seubert et al.
(Continued)

FOREIGN PATENT DOCUMENTS

CN    100356925 C    12/2007
CN    104688769 A    6/2015
(Continued)

OTHER PUBLICATIONS

Williams LB, Haydel SE. Evaluation of the medicinal use of clay minerals as antibacterial agents. Int Geol Rev. Jul. 1, 2010;52(7/8): 745-770. doi: 10.1080/00206811003679737. PMID: 20640226; PMCID: PMC2904249. (Year: 2010).*
(Continued)

*Primary Examiner* — Isaac Shomer
*Assistant Examiner* — Bryan James Rego
(74) *Attorney, Agent, or Firm* — McKee, Voorhees & Sease, PLC

(57) ABSTRACT

Medicinal clay compositions and pharmaceutical compositions containing the same are disclosed. The medicinal clay compositions provide a protective barrier for the clay allowing manufacturing, storage and use that protects the medicinal clay from moisture and hydration that would otherwise prematurely activate the clay. The medicinal clay compositions allow use of medicinal clays in various delivery systems and types of therapeutic compositions, including foams, hydrocolloids, electrospinning, films, pastes, and the like. Methods of preparing the medicinal clay compositions and methods of use are also disclosed. Methods of using the medicinal clay compositions, pharmaceutical compositions, and cation sources to reduce microbial populations on a subject and/or remove chloride from exudate from a tissue or organ in need of treatment are also disclosed.

21 Claims, 16 Drawing Sheets

(51) Int. Cl.
  *A61K 33/38* (2006.01)
  *A61P 31/04* (2006.01)
(58) Field of Classification Search
  USPC .......................................................... 424/618
  See application file for complete search history.

(56) References Cited

U.S. PATENT DOCUMENTS

| | | | |
|---|---|---|---|
| 5,470,581 | A | 11/1995 | Grillo et al. |
| 5,744,151 | A | 4/1998 | Capelli |
| 5,935,889 | A | 8/1999 | Murrell et al. |
| 6,042,839 | A | 3/2000 | Lahanas et al. |
| 6,399,092 | B1 | 6/2002 | Hobson et al. |
| 6,420,473 | B1 | 7/2002 | Chittamuru et al. |
| 9,095,542 | B2 | 8/2015 | Zheng et al. |
| 9,675,077 | B2 | 6/2017 | Parson |
| 9,707,180 | B2 | 7/2017 | Sackler |
| 9,993,421 | B2 | 6/2018 | McPherson et al. |
| 10,046,079 | B2 | 8/2018 | Mukhopadhyay et al. |
| 10,105,388 | B2 | 10/2018 | Kaestner |
| 11,090,366 | B2 | 8/2021 | LoVetri et al. |
| 11,103,433 | B2 | 8/2021 | Gawande et al. |
| 11,124,897 | B1 | 9/2021 | Abudula et al. |
| 2004/0157766 | A1 | 8/2004 | Embil et al. |
| 2005/0019390 | A1 | 1/2005 | Kohnke |
| 2005/0152955 | A1 | 7/2005 | Akhave et al. |
| 2006/0013893 | A1 | 1/2006 | Stockel |
| 2008/0026079 | A1* | 1/2008 | Carpenter ............... A61P 43/00 424/684 |
| 2008/0254112 | A1 | 10/2008 | Klokkers et al. |
| 2009/0017078 | A1 | 1/2009 | Buderer et al. |
| 2010/0130910 | A1 | 5/2010 | Berenson |
| 2010/0137249 | A1 | 6/2010 | Wang et al. |
| 2010/0256369 | A1 | 10/2010 | Suga et al. |
| 2010/0291093 | A1 | 11/2010 | Janda et al. |
| 2012/0219497 | A1 | 8/2012 | Wellisz et al. |
| 2013/0004544 | A1 | 1/2013 | Metge et al. |
| 2013/0317094 | A1 | 11/2013 | Mathee et al. |
| 2016/0200634 | A1 | 7/2016 | Zaseybida et al. |
| 2016/0263007 | A1 | 9/2016 | Strand et al. |
| 2018/0021374 | A1* | 1/2018 | Tuba ..................... A61K 9/0014 424/489 |
| 2018/0125808 | A1* | 5/2018 | Ala'Aldeen ........... A23K 50/10 |
| 2019/0054185 | A1* | 2/2019 | Abduljauwad ......... A61P 35/04 |
| 2019/0256431 | A1 | 8/2019 | Zaseybida et al. |
| 2020/0276458 | A1 | 9/2020 | Daniels |
| 2021/0046186 | A1* | 2/2021 | McCord .................. A61K 47/10 |
| 2021/0106717 | A1 | 4/2021 | Gittard et al. |
| 2021/0121575 | A1 | 4/2021 | Salamone et al. |
| 2021/0253804 | A1* | 8/2021 | Spina ..................... C09D 183/04 |
| 2022/0298208 | A1 | 9/2022 | West et al. |
| 2022/0313571 | A1 | 10/2022 | Hu et al. |
| 2023/0131873 | A1 | 4/2023 | McCord et al. |

FOREIGN PATENT DOCUMENTS

| | | |
|---|---|---|
| EP | 2262535 B1 | 7/2013 |
| GB | 922673 A | 4/1963 |
| KR | 20160012257 A | 2/2016 |
| WO | 9618300 A2 | 6/1996 |
| WO | 2009055312 A1 | 4/2009 |
| WO | 2012131476 A1 | 10/2012 |

OTHER PUBLICATIONS

Ratzke C, Gore J. Modifying and reacting to the environmental pH can drive bacterial interactions. PLoS Biol. Mar. 14, 2018;16(3): e2004248. doi: 10.1371/journal.pbio.2004248. PMID: 29538378; PMCID: PMC5868856. (Year: 2018).*
Kuo, Shu-Hua et al. "Role of pH Value in Clinically Relevant Diagnosis." Diagnostics (Basel, Switzerland) vol. 10,2 107. Feb. 16, 2020, doi: 10.3390/diagnostics10020107 (Year: 2020).*
Nien, Yung-Tang, Yi-Han Liao, and Pao-Chi Liao. "Antibacterial activity of poloxamer-modified montmorillonite clay against E. coli." Materials Letters 65.19-20 (2011): 3092-3094 (Year: 2011).*
Cosmetics Info, "Poloxamer 188." Cosmetics Info, Sep. 22, 2021, cosmeticsinfo.org/ingredient/poloxamer-188 (Year: 2021).*
Seema, S., and M. J. E. C. B. Datta. "Organoclay Pluronic F68— Montmorillonite, as a sustained release drug delivery vehicle for propranolol hydrochloride." Eur. Chem. Bull 3.6 (2014): 593-604 (Year: 2014).*
International Search Report and Written Opinion in PCT/US2022/078579, mailed on Mar. 14, 2023, 20 pages.
Khan et al., "3-Hydroxytyrosol regulates biofilm growth in Cunninghamella elegans," Fungal Biology, Mar. 2021, vol. 125, No. 3, pp. 211-217.
Morrison, Keith D., "Unearthing the Antibacterial Activity of a Natural Clay Deposit," Arizona State University, Oct. 27, 2015, https://core.ac.uk/download/pdf/79581765.pdf, Abstract, 7 pages.
Achenie et al., "Modelling of Drug Release from a Polymer Matrix System," Novel Approaches in Drug Designing & Development, 2017, vol. 2, No. 3, 10 pages.
Bae et al., "Enhanced regenerative healing efficacy of a highly skin-permeable growth factor nanocomplex in a full-thickness excisional mouse-wound model," International Journal of Nanomedicine, 2014, vol. 9, pp. 4551-4567.
Banim, J., "'Trojan Horse' Drug That Kills Cancer Without Damaging Nearby Tissue Successfully Tested," Unilad, Jun. 2021. Retrieved form the Internet: <URL:https://www.unilad.com/technology/scientific-breakthrough-kills-cancer-cells-in-mice>, 6 pages.
Behroozian, S., "Antimicrobial Properties of Kisameet Clay, a Natural Clay Mineral From British Columbia, Canada," Doctoral Thesis, The University of British Columbia, Aug. 2019, 211 pages.
Bodratti et al., "Formulation of Poloxamers for Drug Delivery," Journal of Functional Biomaterials, 2018, vol. 9, No. 11, 24 pages.
Bowler et al., "Combatting wound biofilm and recalcitrance with a novel anti-biofilm Hydrofiber wound dressing," Wound Medicine, 2016, vol. 14, pp. 6-11.
Chen et al., "Mechanical, Rheological and Release Behaviors of a Poloxamer 407/Poloxamer 188/Carbopol 940 Thermosensitive Composite Hydrogel," Molecules, 2013, vol. 18, pp. 12415-12425.
CPI Wurster Process, Coating Place, Inc., 2021. Retrieved from the Internet <URL:https://www.coatingpalce.com>, 3 pages.
Dumortier et al., "A Review of Poloxamer 407 Pharmaceutical and Pharmacological Characteristics," Pharmaceutical Research, 2006, vol. 23, pp. 2709-2728.
Ellison, E., "Controlled Release Nitrogen Fertilizers for Agriculture," Agrium Advanced Technologies, date unknown, 31 pages.
Essential Oils Containing Farnesol, Online Product Listing, New Directions Aromatics Inc., Copyright 1997-2021, 2 pages.
FDA Executive Summary: Classification of Wound Dressings Combine with Drugs, Prepared for the Meeting of the General and Plastic Surgery Devices Advisory Panel, Sep. 2016, 83 pages.
Giuliano et al., "Mucosal Applications of Poloxamer 407-Based Hydrogels: An Overview," Pharmaceutics, 2018, vol. 10, No. 159, 26 pages.
Hagemann, H., "Healing Power of Clay? Not as Off-the-Wall as You Might Think," Eos, 2018, vol. 99, 4 pages.
International consensus, "Appropriate use of silver dressings in wounds. An expert working group consensus, " London: Wounds International, 2012, 24 pages.
Jung et al., "Potential Anti-Inflammatory and Anti-Cancer Properties of Farnesol," Molecules, 2018, vol. 23, No. 2827, 15 pages.
Khandelwal et al., "A surfactant polymer wound dressing protects human keratinocytes from inducible necroptosis," Scientific Reports, 2021, vol. 11, No. 4357, 15 pages.
Kolasinac et al., "Solubility enhancement of desloratadine by solid dispersion in poloxamers," International Journal of Pharmaceutics, 2012, vol. 436, pp. 161-170.
Kvitek et al., "Effect of Surfactants and Polymers on Stability and Antibacterial Activity of Silver Nanoparticles (NP)s," The Journal of Physical Chemistry C, 2008, vol. 112, pp. 5825-5834.
Maisanaba et al., "Toxicological evaluation of clay minerals and derived nanocomposites: A review," Environmental Research, 2015, vol. 138, pp. 233-254.

(56) References Cited

OTHER PUBLICATIONS

McDowell, T.L., "Benzethonium chloride method for proteins adapted to centrifugal analysis," Clinical Chemistry, Jun. 1985, vol. 31, No. 6, pp. 864-866, 1 page.

Miller, R., "Our Geological Wonderland: Blue clay," The Independent, Sep. 9, 2018. Retrieved from the Internet: <URL: https://suindependent.com/geological-wonderland-blue-clay-chinle-formation/>, 12 pages.

Mishra et al., "Development and characterization of pectin/gelatin hydrogel membranes for wound dressing," International Journal of Plastics Technology, Jun. 2011, vol. 15, No. 1, pp. 82-95.

Morrison et al., "Synthetic antibacterial minerals: harnessing a natural geochemical reaction to combat antibiotic resistance," Scientific Reports, 2022, vol. 12, No. 1218, 11 pages.

Nowacka et al., "Farnesol-Containing Macromolecular Systems for Antibiofilm Strategies," Surfaces, 2020, vol. 3, pp. 197-210.

Oh et al., "The I reparation of I olyurethane Foam Combined with pH-sensitive Alginate/Bentonite Hydrogel for Wound Dressings," Fibers and I olymers, 2011, vol. 12, No. 2, pp. 159-165.

Percival et al., "Mode of action of poloxamer-based surfactants in wound care and efficacy on biofilms," International Wound Journal, 2018, vol. 15, pp. 749-755.

Potassium Chloride Extended-Release Capsules, USP, 8mEq and 10 mEq, Prescription Product Information, dated Oct. 14, 2009, 2 pages.

Qureshi et al., "Polysaccharide based superabsorbent hydrogels and their methods of synthesis: A review," Carbohydrate Polymer Technologies and Applications 1, 2020, No. 100014, 14 pages.

Ramage et al., "Inhibition on Candida albicans biofilm formation using divalent cation chelators EDTA," Mycopathologia, 2007, vol. 164, No. 301, 10 pages.

Ricci et al., "Sustained release of lidocaine from Poloxamer 407 gels," International Journal of Pharmaceutics, Jan. 2005, vol. 288, No. 2, pp. 235-244, 2 pages.

Sambale et al., "Investigations of the Toxic Effect of Silver Nanoparticles on Mammalian Cell Lines," Journal of Nanomaterials, 2015, vol. 2015, No. 136765, 10 pages.

Svensson et al., "Kisameet Glacial Clay: an Unexpected Source of Bacterial Diversity," mBio, 2017, vol. 8, Issue 3, 30 pages.

Tian et al., "Controlled drug delivery for glaucoma therapy using montmorillonite/Eudragit microspheres as an ion-exchange carrier," International Journal of Nanomedicine, 2018, vol. 13, pp. 415-428.

Tiefenbacher et al., Maltodextrin—an overview, Various abstracts, ScienceDirect, 8 pages.

Treter et al., "Washing-resistant surfactant coated surface is able to inhibit pathogenic bacteria adhesion," Applied Surface Science, 2014, vol. 303, pp. 147-154.

Urban-Morlan et al., "Determination of poloxamer 188 and poloxamer 407 using high-performance thin-layer chromatography in pharmaceutical formulations," Journal of Pharmaceutical and Biomedical Analysis, Mar. 2008, vol. 46, Issue 4, pp. 799-803, 2 pages.

Wang et al., "Effects of montmorillonite clay on growth performance, nutrient digestibility, vulva size, faecal microflora, and oxidative stress in weaning gilts challenged with zearalenone," Animal Feed Science and Technology, Dec. 2012, vol. 178, Issues 3-4, pp. 158-166, 2 pages.

White et al., "Water-Sorption Characteristics of Clay Minerals," Illinois State Geological Survey, 1959, Circular 266, 24 pages.

Williams et al., "Evaluation of the medicinal use of clay minerals as antibacterial agents," Author Manuscript, International Geology Review, 2010, vol. 52, Nos. 7-8, pp. 745-770.

Williams, L.B., "Geomimicry: harnessing the antibacterial action of clays," Clay Minerals, 2017, vol. 52, 24 pages.

Parrintaj et al., "Poloxamer: A versatile tri-block copolymer for biomedical applications," Acta Biomaterialia, 2020, vol. 110, pp. 37-67, 32 pages.

Afriyie-Gyawu, E., "Safety and Efficacy of Novasil Clay as a Dietary Supplement to Prevent Aflatoxicosis," Texas A&M University, Dec. 2004, Doctoral Thesis, pp. 1-191.

Aslam et al., "Combination of Tigecycline and N-Acetylcysteine Reduces Biofilm-Embedded Bacteria on Vascular Catheters," Antimicrobial Agents and Chemotherapy, Apr. 2007, vol. 51, No. 4, pp. 1556-1558.

Aslam et al., "Role of Antibiofilm-Antimicrobial Agents in Control of Device-Related Infections," International Journal of Arificial Organs, 2011, vol. 34, No. 9, pp. 752-758.

Banai et al., "Influence of Extracellular Magnesium on Capillary Endothelial Cell Proliferation and Migration," Circulation Research, Sep. 1990, vol. 67, No. 3, pp. 645-650.

Becker, L., "Safety Assessment of Glycerin as Used in Cosmetics," Cosmetic Ingredient Review, 2014, pp. 1-32.

Caflisch et al., "Antibacterial activity of reduced iron clay against pathogenic bacteria associated with wound infections," International Journal of Antimicrobial Agents, 2018, vol. 52, pp. 692-696.

Carretero, M., "Clay minerals and their beneficial effects upon human health. A review," Applied Clay Science, 2002, vol. 21, pp. 155-163.

Chen et al., "Hydroxytyrosol prevents dermal papilla cells inflammation under oxidative stress by inducing autophagy," Journal of Biochemical and Molecular Toxicology, 2019, pp. 1-9.

Chowdhury et al., "Pluronic Nanotechnology for Overcoming Drug Resistance," in: Yan et al., Bioactivity of Engineered Nanoparticles, Springer Nature Singapore Pte Ltd., 2017, pp. 207-237.

Cinar, D., "Purification and Antimicrobial Properties of Oleuropein," Thames Valley University, Apr. 2009, Doctoroal Thesis, pp. 1-199.

Costa et al., "N-acetylcysteine-functionalized coating avoids bacterial adhesion and biofilm formation," Scientific Reports, Dec. 12, 2017, vol. 7, No. 17374, pp. 1-13.

CPKelco, "Kelco-Vis DG Diutan Gum: Guidelines for Proper Dissolution," CP Kelco U.S., Inc., 2017, 2 pages.

Cunningham et al., "pH-Dependent Metal Ion Toxicity Influences the Antibacterial Activity of Two Natural Mineral Mixtures," PLoS ONE, vol. 5, No. 3, pp. 1-10.

Damrau, F., "The Value of Bentonite for Diarrhea," Digestive Health, 1961, pp. 1-11.

El-Feky et al., "Effect of Ciprofloxacin and N-acetylcysteine on Bacterial Adherence and Biofilm Formation on Ureteral Stent Surfaces," Polish Journal of Microbiology, 2009, vol. 58, No. 3, pp. 261-267.

Gaskell et al., "Antimicrobial clay-based materials for wound care," Future Medicinal Chemistry, Jun. 4, 2014, Abstract, vol. 6, No. 6, pp. 1-2.

Ghadiri et al., "Biomedical Applications of Cationic Clay Minerals," RSC Advances, 2015, pp. 1-20.

Ghalandari et al., "Antimicrobial effect of Hydroxytyrosol, Hydroxytyrosol Acetate and Hydroxytyrosol Oleate on *Staphylococcus aureus* and *Staphylococcus epidermidis*," Electronic Journal of General Medicine, 2018, pp. 1-7.

Honnegowda et al., "Role of angiogenesis and angiogenic factors in acute and chronic wound healing," Plastic and Aesthetic Research, Sep. 15, 2015, vol. 2, No. 5, pp. 243-249.

Lansdown et al., "Zinc in wound healing: Theoretical, experimental, and clinical aspects," Wound Repair and Regeneration, 2007, vol. 15, pp. 2-16.

Lansdown, A., "Calcium: a potential central regulator in wound healing in the skin," Wound Repair and Regeneration, 2002, Abstract, vol. 10, No. 5, pp. 1-14.

Lin et al., "Zinc in Wound Healing Modulation," Nutrients, 2018, vol. 10, No. 16, pp. 1-20.

Mogen et al., "Pluronics-Formulated Farnesol Promotes Efficient Killing and Demonstrates Novel Interactions with *Streptococcus mutans* Biofilms," PLOS ONE, Jul. 29, 2015, pp. 1-18.

Moloughney et al., "Poloxamer 188 (P188) as a Membrane Resealing Reagent in Biomedical Applications," Recent Patents on Biotechnology, Dec. 2012, vol. 6, No. 3, pp. 200-211.

Moosavi, M., "Bentonite Clay as a Natural Remedy: A Brief Review," Iranian Journal of Public Health, Sep. 2017, vol. 46, No. 9, pp. 1176-1183.

Morrison et al., "Interactions between antibacterial clays and bacteria: Determining the reactivity and geochemistry of transition metals," 2012 Clay Minerals Society Annual Meeting, 2012, Golden, Co., pp. 1-33.

(56) References Cited

OTHER PUBLICATIONS

Morrison et al., "Mineralogical variables that control the antibacterial effectiveness of a natural clay deposit," Environmental Geochemistry and Health, 2014, vol. 36, pp. 613-631.
Morrison et al., "The Anatomy of an Antibacterial Clay Deposit: A New Economic Geology," Economic Geology: Bulletin of the Society of Economic Geologists, Nov. 2017, vol. 112, No. 7, pp. 1551-1570.
Morrison, K. D., "Unearthing the Antibacterial Activity of a Natural Clay Deposit," Arizona State University, Dec. 2015, Doctoral Thesis, pp. 1-180.
Mousa et al., "Clay nanoparticles for regenerative medicine and biomaterial design: A review of clay bioactivity," Biomaterials, 2018, vol. 159, pp. 204-214.
Mousavi et al., "Development of Clay Nanoparticles Toward Bio and Medical Applications," IntechOpen, 2018, pp. 1-26.
Novasil Plus, BASF SE, 2015, 2 pages.
Okano et al., "Inhibition and Induction of Quorum Sensing Using Complexes between N-Acylhomoserine Lactone and Self-assembled Polymer Micelles," Chemistry Letters, 2015, vol. 44, pp. 1544-1546.
Omar, S., "Oleuropein in Olive and its Pharmacological Effects," Scientia Pharmaceutica, 2010, vol. 78, pp. 133-154.
Patel et al., "Poloxamers: A pharmaceutical excipients with therapeutic behaviors," International Journal of PharmTech Research, 2009, vol. 1, No. 2, pp. 299-303.
Phrixus Pharmaceuticals Inc., "Preclinical Safety Results," phrixuspharmaceuticals.com, 2019. Retrieved from the Internet <URL:www.phrixuspharmaceuticals.com/?page_id=190>, 2 pages.
Pray, L., "Antibiotic Resistance, Mutation Rates and MRSA," Nature Education, 2008, vol. 1, No. 1, pp. 1-4.
Rondeau, V., "A review of epidemiologic studies on aluminum and silica in relation to Alzheimer's disease and associated disorders," Reviews on Environmental Health, 2002, vol. 17, No. 2, pp. 107-121.
Sarsour et al., "MnSOD activity regulates hydroxytyrosol-induced extension of chronological lifespan," AGE, 2012, vol. 34, pp. 95-109.
Schumann, K., "Safety Aspects of Iron in Food," Annals of Nutrition and Metabolism, 2001, Abstract, vol. 45, 2 pages.
Serena et al., "Nutrition in patients with chronic non-healing ulcers:a paradigm shift in wound care," Chronic Wound Care Management and Research, 2018, vol. 5, pp. 5-9.
Sircar et al., "High Performance Liquid Chromatography Analysis and Anti-Methicillin Resistant *Staphylococcus aureus* Activity of Olive Fruit Ethanolic Extract," International Research Journal of Pharmacy, 2017, vol. 8, No. 7, pp. 126-130.
Sudjana et al., "Antimicrobial activity of commercial Olea europaea (olive) leaf extract," International Journal of Antimicrobial Agents, 2009, vol. 33, pp. 461-463.
The United States Pharmacopeial Convention, "Glycerin," May 1, 2009, pp. 1-2.
U.S Department of Health and Human Services Public Health Service Agency for Toxic Substances and Disease Registry, "ToxGuide for Aluminum AI," Sep. 2011, 2 pages.
Viseras et al., "Clay Minerals in Skin Drug Delivery," Clay and Clay Minerals, Apr. 5, 2019, Abstract, vol. 67, pp. 59-71.
Wei et al., "Phloretin inhibits biofilm formation by affecting quorum sensing under different temperature," LWT, Sep. 2020, Abstract, vol. 131, No. 109668, pp. 1-2.
Williams et al., "Bentonite, Bandaids, and Borborygmi," Elements, Apr. 1, 2009, vol. 5, No. 2, pp. 1-14.
Williams et al., "Killer Clays! Natural antibacterial clay minerals," Mineralogical Society Bulletin, Apr. 2004, pp. 1-8.
Williams et al., "What makes a Natural Clay Antibacterial?," Environmental Science & Technology, Apr. 15, 2011, vol. 45, No. 8, pp. 3768-3773.
Xu et al., "Rheological properties and thickening mechanism of aqueous diutan gum solution: Effects of temperature and salts," Carbohydrate Polymers, 2015, vol. 132, pp. 620-629.
Park S, Murthy PK, Park S, Mohan YM, Koh WG. Preparation of silver nanoparticle-containing semi-interpenetrating network hydrogels composed of pluronic and poly (acrylamide) with antibacterial property. Journal of Industrial and Engineering Chemistry. Mar. 25, 2011;17(2):293-7.

\* cited by examiner

COATED MEDICINAL CLAY COMPOSITIONS, PHARMACEUTICAL COMPOSITIONS, AND DELIVERY OF CATION SOURCES AND METHODS OF USE THEREOF

CROSS-REFERENCE TO RELATED APPLICATION

This application claims priority under 35 U.S.C. § 119 to provisional application U.S. Ser. No. 63/262,999 filed Oct. 25, 2021 and U.S. Ser. No. 63/364,657 filed May 13, 2022, both entitled "COATED MEDICINAL CLAY COMPOSITIONS, PREPARATIONS THEREOF AND METHODS OF USE," each of which is herein incorporated by reference in its entirety.

FIELD OF THE INVENTION

The invention relates to medicinal clay compositions and pharmaceutical compositions containing the same for providing medicinal (e.g., anti-pathogenic) compositions. The medicinal clay compositions provide a protective barrier for the medicinal clay allowing manufacturing, storage, delivery and use that protects the medicinal clay from body fluids, water sources, moisture and hydration that would otherwise prematurely activate the clay. The medicinal clay compositions further allow use of medicinal clays in various delivery systems and types of therapeutic compositions, such as film, electro-spun materials, foam, hydrocolloid, hydrogel, gel, alginate gel, gel sheet, emulsion, suspension, paste, cream, ointment, cream, powder, tablet, capsule, enemas, transdermal therapeutic system or dressing or other delivery system impregnated with the medicinal clay composition.

Beneficially the medicinal clay compositions can be combined with various additional components (both active and inert components) to deliver the clays for various applications of use, including for example, topical applications. Methods of preparing the medicinal clay compositions and methods of use are also provided for delivery onto a tissue of the body, including skin and wounds, mucosal cells, intestinal track, ear canal, nasal passages and oral cavities in need of treatment thereof.

The invention further relates to methods of treatment utilizing the medicinal clay compositions, pharmaceutical compositions, and/or cation sources to reduce microbial populations on a subject. The medicinal clay compositions, pharmaceutical compositions, or cation sources can further bind chloride in exudate from tissues or organs in need of treatment. The pharmaceutical compositions utilize the medicinal clay to chelate anions and thereby removing chloride in exudate to prevent premature activation and chelation of therapeutic cations.

Beneficially, the methods described allow the delivery of medicinal clay compositions or the cation sources (which can further deliver a therapeutic agent) to a tissue in need of treatment, such as skin or a wound, without being bound or reacting with organic materials found in such a tissue and thereby preventing delivery to the tissue in need of treatment. Instead, the methods use cations to chelate anions to ensure the medicinal clay or a therapeutic agent provided with a cation source reaches the tissue in need of treatment, without the need to increase the level of a therapeutic agent, such as a therapeutic cation or an antimicrobial agent.

BACKGROUND OF THE INVENTION

The beneficial health effects of clays, including anti-pathogenic properties have been widely researched for current and potential biomedical applications. Clays may be classified or referred to as natural minerals having particulate diameters of <2 µm. Although many natural clays have been studied for their medicinal activities, including antimicrobial effects, only certain clays are anti-pathogenic in clinical applications. Rectorite clays are generally known for a 50:50 illite:smectite ratio and are formed by hydrothermal activity (non-loess) and have been studied for its beneficial antimicrobial effects against a broad spectrum of pathogens, including antibiotic-resistant strains. Rectorite has been studied for its antimicrobial efficacy against pathogens such as Staphylococci, Streptococci, Enterobacteriaceae, and non-fermenting Gram-negative bacilli, to name a few. Rectorite has further been studied for its superior antimicrobial activity against pathogens such as *E. coli* and methicillin-resistant *Staphylococcus aureus* (MRSA).

There is an insufficient and inconsistent characterization of the precise make-up of the medicinal clays. Simply put, it is challenging to reproduce effects unless a correct or precise source of clay is used and can be chemically characterized. However, clays that have been identified as potentially having anti-pathogenic properties share mineralogical and chemical compositions that impact the buffering capacity of fluids in contact with the clay. Specifically, medicinal clays tend to contain significant amounts of reduced transmission metals (most commonly $Fe^{3+}$, $Fe^{2+}$ and $Al^{3+}$) and have the capability of impacting water chemistry due to its chemical/mineralogical makeup, and small particle size (large surface area).

One of the major barriers in working with medicinal clays is preserving the essential physical properties of the material throughout processing, manufacturing, sterilization, packaging, and storage so the finished material maintains adequate levels of activity at the time of use. The activity of clay is influenced by a combination of factors including crystal structure, metal speciation, mineral reactivity, oxidative-reductive potential (ORP), cation exchange capacity (CEC) and pH. Each of those physical characteristics can potentially be altered by processing and storage conditions in a manner that diminishes the anti-pathogenic activity of the clay, so it is essential to establish methods that preserve the structure, function, and activity throughout the process.

The clay crystal structure serves as a reservoir for reduced cations (iron, aluminum, zinc, magnesium, etc.) that can be released into the environment when specific conditions are met. That reservoir of cations is best maintained in an anhydrous and acidic pH environment that prevents the dissolution, leaching, and oxidation of the effective cations. The crystal structures that appear to create the best reservoir involve a combination of smectite and illite in varying proportions.

The balance of illite and smectite may dictate the speed at which reduced cations are released and/or oxidized. Mixed illite-smectite clays with a higher ratio of illite appear to be more resistant to acid dissolution, providing a more protective reservoir for reduced cations essentially slowing the oxidation of cations and creating a natural time-release mechanism. Ideally, the clay material should contain at least 40% of total illite/smectite clay moieties (i.e., combinations of different types of illite, smectite, and/or illite-smectite mixed material).

Soluble cations are essential for the anti-pathogenic activity of medicinal clays. It is thought that Iron ($Fe^+$ and $Fe^{2+}$) and Aluminum ($Al^{3+}$) are responsible for most of the anti-pathogenic activity observed in medicinal clays, however some research has indicated that the activity may not be completely dependent on the chemical identity of the reduced cations, as anti-pathogenic effects have been observed with a variety of combinations of reduced cations as long as the target ORP, CEC, pH and other parameters are adequate. It has been demonstrated that $Al^{3+}$, $Fe^{3+}$ and $Fe^{+}$ exhibit a synergy by targeting different parts of the bacteria with $Al^{3+}$ functioning primarily in membranes and $Fe^{+}/Fe^{+}$ functioning within the intercellular/cytosolic spaces.

While research has demonstrated that application of medicinal clays in their raw form can effectively reduce pathogen population size, there remains a need for developing delivery systems for clay that retain the targeted ORP, CEC, pH, and other parameters to provide stable and medically acceptable (including sterile and effective). For example, an acidic pH (<4.7) is also essential for the release of reduced cations from clay material in high enough concentrations to exhibit anti-pathogenic activity. Clays with a pH<3 that meet the above criteria for CEC and ORP have exhibited the most potent anti-pathogenic activity, however consideration needs to be given to the application of the product to determine if the pH is safe and/or tolerable for that application. Note that calcite and dolomite act as natural buffers and typically raise the pH of clays, subsequently reducing activity. Natural biological buffering systems should also be considered when assessing the properties and applications of medicinal clays. Moisture is a catalyst that allows for the release of cations from medicinal clays, providing the pH is at an appropriate level (<4.7). Every attempt should be made to protect the clay from moisture, or water sources, until the moment of use, as it has a potential to start the activation cascade including the release and oxidation of reduced cations from the clay crystal structure.

To date, effective delivery of clays for applications of use and for the ability to store stable compositions containing clays has not been achieved. Instead, the conventional use of clays includes the mixing of clay with water to form a commercial paste or gel that is simply applied externally. This type of preparation does not protect the required anti-pathogenic properties of the clay material and results in the premature activation of the clay, rapidly diminishing and even completely exhausting the anti-pathogenic activity long before it reaches its intended target. This traditional method of preparation significantly limits the effective use of anti-pathogenic clays in various settings.

Additionally, the clinical delivery of active anti-pathogenic clay must take into consideration that the clay material cannot be hydrated until the moment of intended use, and fine particulate powders with <100 micron particles cannot be used in a healthcare setting due to inhalation concerns, and further bedside compounding (mixing water and clay before application) is severely restricted by federal law. Therefore, it is necessary that clay preparations be provided in a non-aqueous delivery system that prevents aerosolization of fine particulate matter, yet also does not require bedside compounding. While the clay is in a non-aqueous system, it must remain miscible/permeable with aqueous environments to allow for proper hydration and activation of the clay particles.

Still further various products and disclosures that refer to treating biofilms and other wounds may use a combination of antimicrobial metal ion (e.g. silver), other cationic surfactant (e.g. benzethonium chloride), and/or chelants such as ethylenediaminetetra-acetic acid (EDTA). However, they fail to address the ability of the antimicrobial metal ion reaching a wound exudate or biofilm. Instead the cation is deactivated and fails to deliver the antimicrobial metal ion. Moreover, EDTA blocks the Fenton reaction from taking place, such that hydroxyl radicals are not generated as the EDTA binds to $Fe^{2+}/Fe^{3+}/Al^{3+}$ instead of allow oxidization through the Fenton reaction. These challenges are illustrated in U.S. Pat. Nos. 9,675,077, 11,090,366, and 11,103,433 and the compositions and methods described according to the disclosure overcome these challenges.

It is therefore an object of this disclosure to provide medicinal clay compositions for utilizing anti-pathogenic clays for various applications of use to take advantage of the medicinal applications of use for clays while protecting the clay from activation before application and in body fluids to a site in need of treatment.

It is a further object of the disclosure to provide pharmaceutical compositions containing medicinal clay compositions to provide stable and medically acceptable (including sterile and effective) compositions in various delivery forms.

It is a further object of the disclosure to provide pharmaceutical compositions containing medicinal clay compositions and a therapeutic agent, such as a therapeutic cation (e.g., silver) to provide effective delivery of the therapeutic cation in various delivery forms that survives wound exudate and other harsh conditions that conventionally inactivate the therapeutic agent.

It is a still further object of the disclosure to provide pharmaceutical compositions containing a medicinal clay composition to provide safe an effective dosing of clay to ensure constituent ingredients in drugs (21 CFR 610.15) are provided for various applications of use.

It is a further object of the disclosure to provide pharmaceutical compositions containing a medicinal clay composition for reducing antibiotic resistance by effectively eliminating difficult to treat pathogens.

It is another object of this disclosure to formulate methods of providing medicinal clay compositions.

It is a still further object of the disclosure to provide methods of using the medicinal clay compositions, pharmaceutical compositions containing the medicinal clay compositions, as well as a cation source to aid in the delivery of a therapeutic agent to reduce microbial populations on a subject and/or remove chloride from exudate in a tissue or organ in need of treatment.

SUMMARY OF THE INVENTION

The present disclosure utilizes the effects of medicinal clay to treat pathogens at a site of infection (e.g., wound tissue or organ that is infected and in need of treatment). As described herein according to embodiments the clay is embedded within a coating and/or surrounded by a coating, which maintains at least the ORP, CEC, and pH of the clay within set specifications, as defined herein, to assure anti-pathogenic activity remains within viable ranges. Beneficially, the coated clay is stable and prevents the activation of the clay until a point of use or treatment at the site, where the activation of the clay results in the release of elements such as iron (particularly reduced $Fe^{+}$ and $Fe^{2+}$) and aluminum (particularly $Al^{3+}$), where both elements damage pathogen membranes. The damaging of the membranes then allows for the excess iron to cause intracellular protein damage through oxidation. Further, not only does the clay target pathogens, but the clay also absorbs toxins. According to the methods of treatment, the clay is further used to remove oils, secretions, toxins, and contaminants from the treated surface, such as a tissue or organ of the body.

Accordingly, in a first aspect medicinal clay compositions are provided.

In another aspect, pharmaceutical compositions containing the medicinal clay compositions are provided.

In another aspect, methods of making or providing medicinal clays are provided.

In still further aspects, methods of treatment using the medicinal clay compositions and/or pharmaceutical compositions are provided. Beneficially, the treatment using the medicinal clay compositions and/or pharmaceutical compositions provide an effective delivery vehicle for an electrolyte sensitive material to contact the body fluid milieu. For example, the presence of significant amounts of chloride in bodily fluids (e.g., exudate) makes it difficult for conventional wound treatments to work, such as a therapeutic cation. An exemplary therapeutic cation is silver. Beneficially, the compositions described herein provide clay in a coated system that maintains desired Cation Exchange Capacity of at least about 10 mEq/100 g, an Oxidation-Reduction Potential greater than about 250 mV, and a pH less than about 5.0. This protects the clay from premature ion discharge (i.e., activation) and further provides time-release capabilities.

According to the various aspects described herein, compositions and methods that deliver clay within a system that can reach and kill the target pathogens, reduce biofilms and contain an internal buffering system (in some embodiments) result in effective formulation, delivery and therapeutic use.

According to further aspects, methods of treatment using a cation source to aid in delivery of a therapeutic agent are provided. Beneficially, the treatment using a cation source allows the delivery of a therapeutic agent to a tissue in need of treatment, such as skin or a wound, without being bound or reacting with organic materials found in such a tissue and thereby preventing delivery to the tissue in need of treatment. Instead, the treatment uses cation sources to chelate chloride (i.e. anions) to ensure the therapeutic agent accompanying the cation source reaches the tissue in need of treatment, without the need to increase the level of a therapeutic agent, such as a therapeutic cation or an antimicrobial agent.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
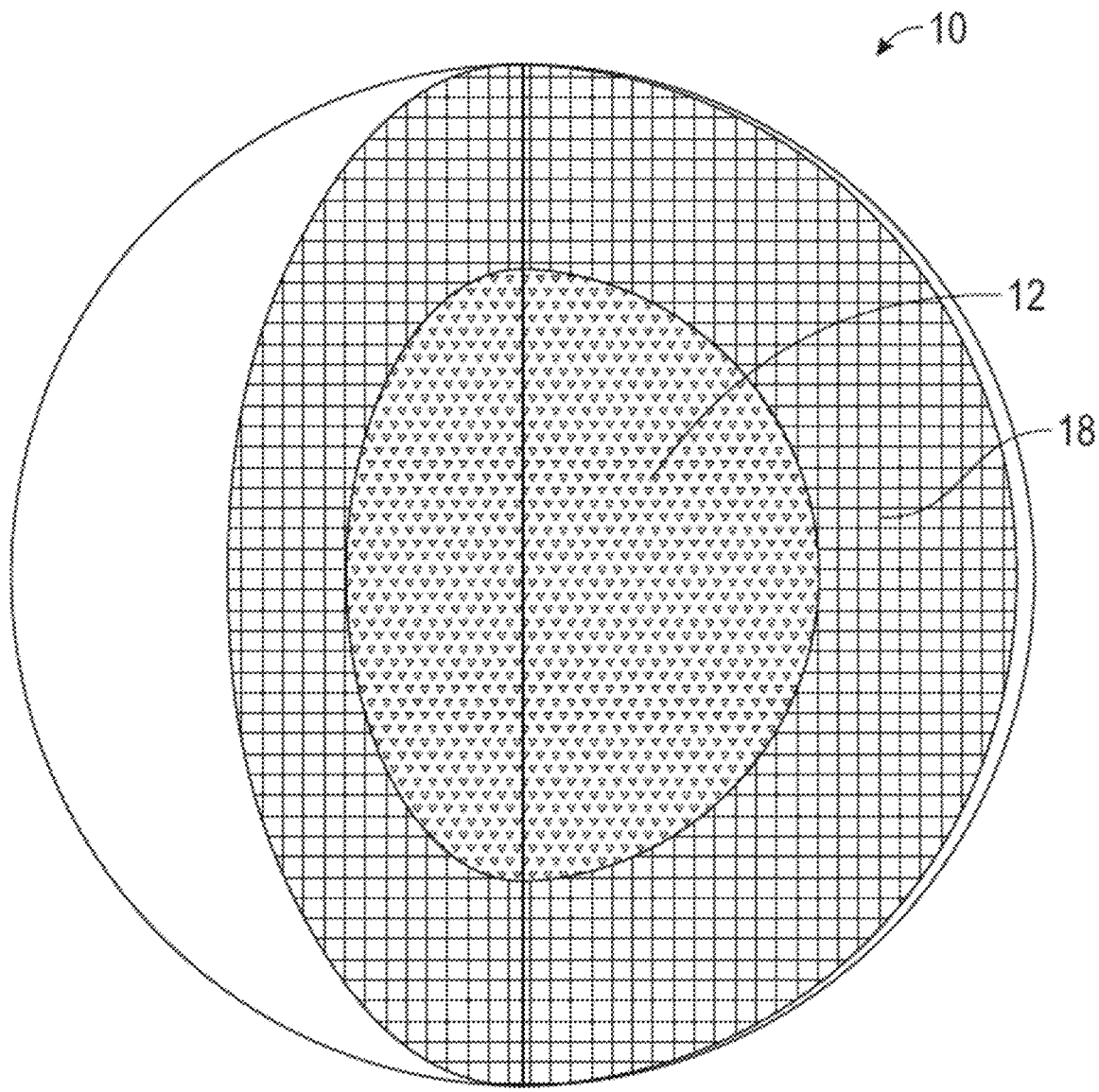
FIGS. 1-5 show exemplary sphere-shaped medicinal clay compositions according to embodiments of the disclosure.

Various embodiments of the present disclosure will be described in detail with reference to the drawings, wherein like reference numerals represent like parts throughout the several views. Reference to various embodiments does not limit the scope of the disclosure. Figures represented herein are not limitations to the various embodiments according to the disclosure and are presented for exemplary illustration of the disclosure. An artisan of ordinary skill in the art need not view, within isolated figure(s), the near infinite number of distinct permutations of features described in the following detailed description to facilitate an understanding of the present disclosure.

DETAILED DESCRIPTION

The embodiments are not limited to particular clay compositions, methods of making the clay compositions, and methods of use thereof, which can vary and are understood by skilled artisans. It has been surprisingly found that the clay compositions beneficially provide clays in a stable delivery system expanding the opportunity going use clays for treatments and care of various tissues of the body, including skin, mucosal membranes and organs in need of treatment thereof.

It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers within the defined range. Throughout this disclosure, various aspects are presented in a range format. It should be understood that the description in range format is merely for convenience and brevity and should not be construed as an inflexible limitation on the scope of the disclosure and the invention. Accordingly, the description of a range should be considered to have specifically disclosed all the possible sub-ranges as well as individual numerical values within that range (e.g., 1 to 5 includes 1, 1.5, 2, 2.75, 3, 3.80, 4, and 5).

As used herein, the term "and/or", e.g., "X and/or Y" shall be understood to mean either "X and Y" or "X or Y" and shall be taken to provide explicit support for both meanings or for either meaning, e.g., A and/or B includes the options i) A, ii) B or iii) A and B.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

So that the present disclosure may be more readily understood, certain terms are first defined. Unless defined otherwise, all technical and scientific terms used herein have the same meaning as commonly understood by one of ordinary skill in the art to which embodiments of the disclosure pertain. The definitions are provided to aid in describing particular embodiments, and are not intended to limit the claimed invention, because the scope of the invention is limited only by the claims. Many methods and materials similar, modified, or equivalent to those described herein can be used in the practice of the embodiments without undue experimentation, but the preferred materials and methods are described herein. In describing and claiming the embodiments, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "anti-pathogenic" is defined herein to mean a composition that inhibits the growth of, or kills, organisms including pathogens, protozoans, viruses, yeast, fungi, or other infectious agents.

The terms "include" and "including" when used in reference to a list of materials refer to but are not limited to the materials so listed.

As used herein, the term "exemplary" refers to an example, an instance, or an illustration, and does not indicate a most preferred embodiment unless otherwise stated.

As used herein, the term "free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%. Still further the amount of the component is 0 wt-%.

As used herein, the term "treat", "treated", "treatment", "treating" or like terms when used with respect to a disease or disorder refers to a therapeutic or prophylactic treatment that increases the resistance of a subject to development of the disease (e.g., to infection with a pathogen, such as a bacteria or fungus), that decreases the likelihood that the subject will develop the disease (e.g., become infected with the pathogen), that increases the ability of a subject that has developed disease (e.g., a pathogenic [e.g., fungal] infection) to fight the disease (e.g., reduce or eliminate at least one symptom typically associated with the infection) or prevent the disease from becoming worse, or that decreases, reduces, or inhibits at least one function of the pathogen, and/or to grow by at least 10% (e.g., at least 20%, 30%, 40%, 50%, 60%, 70%, 80%, 90%, 95%, or 100%). In some embodiments, "treat," "treated," "treatment" or "treating" refers to a therapeutic or prophylactic treatment that reduces microbial populations on a tissue that is infected.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions may comprise, consist essentially of, or consist of the components and ingredients as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Medicinal Clay Compositions

According to embodiments, the medicinal clay compositions prevent the clay from premature activation from hydration. Beneficially the medicinal clay compositions provide stable compositions. The medicinal clay compositions include at least one source of clay and at least one coating agent. The medicinal clay compositions can further include additional functional ingredients. The pharmaceutical compositions include the medicinal clay compositions and further include additional therapeutic agents, additional functional ingredients, and/or delivery systems. Exemplary medicinal clay compositions are shown in Table 1 and pharmaceutical compositions containing the medicinal clay compositions are shown in Table 2, both in weight percentage. While the components may have a percent actives of 100%, it is noted that the Tables do not recite the percent actives of the components, but rather, recites the total weight percentage of the raw materials (i.e., active concentration plus inert ingredients).

Although the compositions described herein delivery a medicinal clay for would treatments and other therapeutic applications, the coatings employed can beneficially provide delivery systems for clay and other material that activates bactericidal activity by ion exchange and are affected by electrolytes (e.g., silver).

TABLE 1

Medicinal Clay Compositions

| Material | First Exemplary Range wt.-% | Second Exemplary Range wt.-% | Third Exemplary Range wt.-% |
| --- | --- | --- | --- |
| Medicinal Clay | 10-90 | 20-80 | 20-70 |
| Coating agent (e.g., Polymers, Polysaccharides, Mineral Salts) | 10-90 | 20-80 | 30-80 |
| Additional Functional Ingredients (e.g, Buffers, Binders, Biofilm inhibitors) | 0-70 | 0-50 | 0-25 |

TABLE 2

Pharmaceutical Compositions

| Material | First Exemplary Range wt.-% | Second Exemplary Range wt.-% | Third Exemplary Range wt.-% |
| --- | --- | --- | --- |
| Medicinal Clay Compositions | 1-70 | 1-50 | 5-50 |
| Additional Therapeutic Agents | 0-80 | 0.1-80 | 1-50 |
| Additional Functional Ingredients | 30-99 | 50-99 | 50-95 |

The medicinal clay compositions described herein can have one or more coated layers of clay (and/or additional therapeutic agents) disposed therein. The medicinal clay compositions can further include one or more buffer systems coated therein. The number of layers of coating and the thickness of the coatings can vary, such as described and depicted herein. In some embodiments the total size of the medicinal clay compositions is at least about 20 microns, at least about 40 microns, at least about 50 microns, at least about 100 microns, or greater. Such variation will depend upon factors including the thickness of the coating(s) as well as the particle size of the clay that is coated. In some embodiments, it is desired to have medicinal clay compositions having a diameter that is from about 1 microns to about 100 microns, or at least about 100 microns.

The medicinal clay compositions beneficially provide for shelf stable compositions for various applications of use, including topical applications. In embodiments, the pharmaceutical compositions containing the medicinal clay compositions (which includes various delivery systems for providing the medicinal clay) are shelf stable for a period of at least about 1 year prior to administration. In other embodiments, the clay delivery systems and compositions are stable for a period of at least about 1 year and 6 months (i.e., 18 months) prior to administration. In further embodiments, the clay delivery systems and compositions are stable for a period of time that is longer than about 1.5 years, or 2 years. In an embodiment the shelf stability is confirmed by retained anti-pathogenic efficacy of the clay as measured by pH, CEC, and ORP (mv) with stability testing being done in accordance with FDA Guidance 21 CFR P211.

As referred to herein the pharmaceutical compositions employ the medicinal clay compositions in combination with additional therapeutic agents, additional functional ingredients and/or in a desired delivery system for a particular application of use. As the medicinal clay compositions themselves are not formulated with extended use of water further formulation into the pharmaceutical composition can provide a desired delivery system or delivery form. In some embodiments, the exposure to water in the coating process is limited to about 48 hours (longer applications such as dissolvable pectin films or also foams require longer to drive off water from the process), or about 24 hours, or about 12 hours, or most preferably about one hour. For example, the pharmaceutical compositions that are foams or hydrocolloids include aqueous or water-containing components and would require subjecting the clay to high temperatures. Beneficially, the pharmaceutical compositions containing the polymers, buffers, binders, and biofilm inhibitor protect the clay from the water-containing components and high heat to provide long-term stability for the clay contained therein. In preferred embodiments the coating process does not expose the clay to water for an extended period of time, and in most applications for less than about one hour.

Exemplary dosage forms for the pharmaceutical compositions can include film, electro-spun materials, foam, hydrocolloid, hydrogel, gel, alginate gel, gel sheet, emulsion, suspension, paste, cream, ointment, cream, powder, tablet, capsule, transdermal therapeutic system or dressing or other delivery system impregnated with the medicinal clay. In an embodiment the pharmaceutical composition can be provided in one or more dosage forms where there is water or an aqueous system in the composition or dosage form (e.g., hydrocolloids with water in the dressing) without activating the medicinal clay as a result of the medicinal clay composition as described herein. In another embodiment the pharmaceutical composition can be provided in a dry dosage form (e.g., powders). In still other embodiments the pharmaceutical composition can be provided in semi-solid dosage forms (e.g., pastes, gellants (e.g., containing alginates), ointments) wherein a greater concentration of the coated medicinal clay composition is included to provide thicker/drier consistencies.

Medicinal Clays

The medicinal clay compositions comprise at least one source of clay. Suitable clays include, but are not limited to, a natural clay or clay mineral and/or synthetic clay or clay mineral, or other suitable materials having clay-like properties, so long as the clay is medicinal and provides effective anti-pathogenic efficacy. In embodiments the medicinal clay compositions are a cation source. In embodiments, a suitable clay includes a blend of minerals and nutrients that cleanse and aid in the antimicrobial effectiveness of silver and other medicants. A combination of clays can be employed as well. Clays include a variety of natural mineral made up of crystalline material. Clay minerals have a sheet-like structure and are composed of mainly silicate and aluminate groups. In some embodiments, the medicinal clays are predominantly layered silicate structures. Exemplary silicate classifications include phyllosilicates (e.g., 2:1 phyllosilicates, 1:1 phyllosilicates (kaolinites and serpentines), etc.), smectite, illite, illite-smectite, kaolinite, and other silicates, e.g., aluminum silicates, magnesium aluminum silicates, magnesium trisilicates, and the like. Various embodiments of the medicinal clays have layered silicate structures as further described herein.

In embodiments the medicinal clays can be hydrated. In further embodiments, the medicinal clays are polycationic compounds. In still further embodiments, the medicinal clays are amorphous and do not have a rigid structure.

In exemplary embodiments, the medicinal clay is a mined medicinal clay. Despite significant reporting of the anti-pathogenic efficacy and medicinal nature of various clays, their physical makeup is highly inconsistent and difficult to reproduce. Applicants describe herein that medicinal clay is dominated by phyllosilicates, namely smectites, illites, and illite-smectite (a group of clay minerals having an expandable interlayer structure). It has been identified that the expandable smectite interlayer region functions like a reservoir from which metals, which may have antimicrobial effects, are slowly released via cation exchange.

In exemplary embodiments, the medicinal clay can be a naturally mined medicinal (namely anti-pathogenic) clay referred to as Fentonite™, wherein the clay is a 2:1 tetrahedral/octahedral phyllosilicate with reduced iron octahedral and exchangeable cations and is therefore capable of catalyzing Fenton reactions, namely catalyzing Fenton reactions within fluids, such as bacterial cytosol and macrophage lysosomes where the medicinal clay will be delivered for the treatment methods described herein. As referred to herein the 2:1 phyllosilicate describes the crystalline structure of the clay itself (2:1 tetrahedral-octahedral-tetrahedral clay) and can include a variety of illites, smectites, and illite-smectite mixed clays (which are referred to as rectorites clays having alternative layers of the illite-smectite), along with other silicates, chlorites, and smectites (e.g., montmorillonites), and the like. The clay having reduced octahedral and exchangeable cations refers to the active component that conveys the medicinal, i.e., antimicrobial, effects, namely the presence of reduced metallic cations in both the interlayer spaces and within the octahedral crystalline layer of the clay (including but not limited to iron, aluminum, and magnesium). The crystalline structure of the clay beneficially holds, protects, and releases the reduced metallic cations under desired conditions, including those delivery conditions described herein.

The clay material (as it will be used for wound care applications) should have a CEC, or amount of cations that can be held in the clay material, as a raw material that needs to be maintained through processing and manufacturing as well as prior to application on the end user. Research indicates that a CEC of greater than 10 mEq/100 grams is needed for anti-pathogenic effect. Typically, the CEC of illite-smectite (I-S) clays varies from about 20-60 mEq/100 g, providing an exchange capacity of 10-20 mM/100 g for divalent cations.

The efficacy of clays is not only dependent on the CEC, but also on the oxidative state of those cations. Soluble reduced cations like $Fe^+$ and $Fe^+$ and $Al^{3+}$ contribute to the non-cytotoxic and anti-pathogenic mechanism of clays by interacting with proteins, enzymes, nucleic acids, and negatively charged (anionic) compounds in the cytosol and membranes of pathogens. In an embodiment, the soluble reduced cations chelate anions. Once inside the pathogen's membranes and cytosol, they become oxidized and contribute to misfolding of proteins, enzyme deactivation, precipitate formation, membrane oxidation, and initiation of redox pathways that produce reactive oxygen species (ROS), namely hydroxyl radicals, that attack pathogenic intracellular proteins and DNA.

Cations must be in their reduced form to exhibit anti-pathogenic effects, so it is essential that metallic cations have not been oxidized before they get to their intended site of action. An ORP/Eh of greater than 250 mV is required for anti-pathogenic effects. In preferred embodiments an ORP from about 300-600 mV is used. Beneficially, the clay provides cations for a non-cytotoxic and anti-pathogenic activity.

An acidic pH (<4.7) is also essential for the release of reduced cations from clay material in high enough concentrations to exhibit anti-pathogenic activity. Clays with a pH <3 that meet the above criteria for CEC and ORP have exhibited the most potent anti-pathogenic activity, however consideration needs to be given to the application of the product to determine if the pH is safe and/or tolerable for that application.

In preferred embodiments, the medicinal clay is referred to as a Fentonite™ medicinal clay, which include phyllosilicates (including for example bentonites, rectorites, and other clays) having one or more of the following product specifications:
Cation Exchange Capacity (CEC)>10 mEq/100 g, preferably from about 10 mEq/100 g to about 100 mEq/100 g;
Oxidation-Reduction Potential (ORP)>250 mV>300 mV, or preferably >400 mV;
pH<5.0 (or between about 2.5 and about 5);
Total Combined Illite/Smectite/I-S>40%;
a 2:1 tetrahedral/octahedral phyllosilicate with reduced iron octahedral and exchangeable cations;
contains at least about 1% pyrite (iron), preferably between about 1-20% pyrite (iron); and/or
Heavy Metals (total)<40 ppm.

In an embodiment the clay has at least two of the product specifications:
Cation Exchange Capacity of at least about greater than about 10 mEq/100 g, preferably from about 10 mEq/100 g to about 100 mEq/100 g;
Oxidation-Reduction Potential greater than about 250 mV, >300 mV, or preferably >400 mV;
pH less than about 5.0 (or between about 3 and about 5);
clay crystalline composition of smectite, illite, and/or illite-smectite, that is at least about 40 wt-% of the clay;
2:1 tetrahedral/octahedral phyllosilicate with reduced iron octahedral and exchangeable cations;
contains at least about 1% pyrite (iron), preferably between about 1-20% pyrite (iron); and
less than 40 ppm heavy metal contaminants.

In a still further embodiment, the clay has at least three, at least four, or all five of these described product specifications.

In still further embodiments the clay has a Cation Exchange Capacity of at least about greater than about 10 mEq/100 g, preferably from about 10 mEq/100 g to about 100 mEq/100 g and an Oxidation-Reduction Potential greater than about 250 mV, >300 mV, or preferably >400 mV. Without being limited to a particular mechanism of action, the clay having the defined CEC and ORP provides a synergy in efficacy of the medicinal clay composition.

In a further embodiment, the medicinal clay composition has at least about 50 wt-% Smectite, Illite, and/or Illite-Smectite. In still further embodiments, the medicinal clay composition has at least about 60 wt-% Smectite, Illite and/or Illite-Smectite. In still further preferred embodiments, any of the medicinal clay compositions described herein also has a cation exchange capacity (CEC) of at least about >10 mEq/100 g, or between about 10 mEq/100 g to about 100 mEq/100 g. The CEC refers to the ability of the clay to hold onto cations (e.g., positively charged ions such as calcium ($Ca^{2+}$), magnesium ($Mg^{2+}$), and potassium ($K^+$), sodium ($Na^+$), silver ($Ag^+$), hydrogen ($H^+$), aluminum ($Al^{3+}$), iron ($Fe^+$ and $Fe^{2+}$), manganese ($Mn^{2+}$), zinc ($Zn^{2+}$) and copper ($Cu^{2+}$)).

In a further embodiment, the medicinal clay has a transition metal combination that includes a level of pyrite ranging from about 1 wt-% to about 10 wt-% or a level of pyrite ranging from about 1 wt-% to about 5 wt-%. Beneficially, the natural minerals can release soluble transition metals at low pH which are effective in killing pathogens due to the generation of reactive oxygen species and damage to pathogen membranes.

The medicinal clay may also be modified with various substituents to alter the properties of the clay. Non-limiting examples of modifications include modification with organic material, polymers, reducing agents, and various elements such as sodium, iron, silver, or bromide, or by treatment with a strong acid. In some embodiments, a medicinal clay of the present disclosure is modified with reducing metal oxides. In preferred alternatives of the embodiments, when a medicinal clay is modified with reducing metal oxides, the medicinal clay is modified with pyrite. In still other embodiments, the medicinal clay is unmodified.

In some embodiments the medicinal clay can also have one or more of the following product specifications: color/appearance that is light tan to blue/gray/green, Smectite concentration between about 10-40%, Illite concentration between about 10-40%, Illite-Smectite (I-S) concentration between about 20-50%, Aluminum ($Al_2O_3$) concentration between about 10-30%, elemental concentration between about 5-15%, Iron (pyrite) concentration between about 4-20%, Iron (III) Oxide concentration between about 0-10%, Sulfur concentration between about 0-20%, Calcite concentration less than about 0.5%, Carbonate concentration less than about 0.5%, and/or Kaolinite concentration less than about 3.5%. Additional disclosure of clays is set forth in Unearthing the Antimicrobial Activity of a Natural Clay Deposit by Keith Morrison, Arizona State University (December 2015); Catalogued Dissertation Presentation, and https://core.ac.uk/download/pdf/4270172.pdf, each of which are herein incorporated by reference in its entirety.

An exemplary source of clay that can be used to provide anti-microbial clays include glacial clays including Kisameet Bay glacial clay. These clays can be modified with various substituents to alter the properties of the clay to the specifications described herein.

In exemplary embodiments, the medicinal clay can also be a synthetic clay that mimics the structure of the clay that provides the anti-pathogenic efficacy against pathogens. Synthetic clays can be used to overcome limitations of natural clays being highly heterogenous. Synthetic clays can have a crystalline composition of smectite, illite, and/or illite-smectite that is at least about 40 wt-% of the clay.

In some embodiments, synthetic clays having anti-pathogenic efficacy and medicinal efficacy should also have the predominate make-up as illite-smectite and pyrite, or smectite and pyrite. In some embodiments, the smectite and pyrite is at least about 75 wt-%, or from about 75-100 wt-% of the clay.

In embodiments, the synthetic clays also have the properties linked to ROS generation. It has been identified by Morrison et al., Nature Portfolio (2022) 12:1218 that pyrites in particular have mineral semi-conductor properties can be linked to ROS generation in solution.

The particle size of the medicinal clay may be an important factor that can affect its effectiveness, as well as bioavailability, blend uniformity, segregation, and flow properties. In general, smaller particle sizes of clay increase its effectiveness by increasing the surface area. In some embodiments, the particle size of the clay is reduced through processes such as milling. In an embodiment, milling can be used to reduce the particle size of clay down to less than 100 microns. In additional embodiments it is desirable to prill the clay, such as prilling into bead-like structures (i.e., prilled beads) for coating according to the disclosure.

In various embodiments, the average particle size of the clay is less than about 250 microns in diameter, less than about 100 microns in diameter, or less than about 90 microns in diameter, or less than about 80 microns in diameter, or less than about 70 microns in diameter, or less than about 60 microns in diameter, or preferably less than about 50 microns in diameter. In some applications, the average particle size of the clay is between about 10 to about 100 microns, between about 10 to about 50 microns, or between about 10 to about 25 microns in diameter. Without being limited to a particular mechanism of processing the clay for the compositions described herein, the clay particles pass through a mesh screen to achieve a uniform desired micron size, as is referred to as clay milling. As opposed to conventional use of a metal ball to aid in the milling, the compositions described herein are produced using a ceramic ball to ensure no metal contaminants are included in the clay delivery systems.

In some embodiments, the medicinal clay is preferably sterilized after formulation into the clay delivery system to kill any environmental microbes in the clay. Methods of sterilization are used that do not negatively impact the stability or anti-pathogenic activity of the coated clay or delivery system. Similarly, in embodiments wherein a reducing agent may be added to an anti-pathogenic clay, the particle size of a reducing agent may also be an important factor that can affect its effectiveness, and in general, smaller particle sizes increase its effectiveness. Preferably, the average particle size of the reducing agent that may be added to an anti-pathogenic clay is less than 100 micron in size.

In some embodiments, the medicinal clay is included in the medicinal clay compositions at an amount of at least about 10 wt-% to about 90 wt-%, about 10 wt-% to about 80 wt-%, about 10 wt-% to about 75 wt-%, about 10 wt-% to about 70 wt-%, about 20 wt-% to about 80 wt-%, about 20 wt-% to about 75 wt-%, or about 20 wt-% to about 70 wt-%. In other embodiments, the medicinal clay is included in the medicinal clay compositions at an amount of at least about 20 wt-% of the composition. In addition, without being limited according to the disclosure, all ranges recited are inclusive of the numbers defining the range and include each integer within the defined range.

Coatings for Medicinal Clay

The medicinal clay is coated with at least one coating agent as described herein to provide stability and delivery benefits. In some embodiments it is desired to formulate a coating or encapsulation that allows delivery of the medicinal clay within a water based system or body fluids, which is known to present stability challenges as the water source or moisture activates the clay. Accordingly, the coating of the clay can provide a time release effect for delivery system in order to maintain integrity of the medicinal clay.

The coating of the clay (or multiple coatings) is based on the particular stressors on the clay for a particular delivery system and/or site of delivery. In some embodiments, multiple layers or coatings can be employed. For example, in an embodiment two or more layers are provided. Beneficially according to the embodiments described herein the medicinal clay compositions provide shelf stability for the medicinal clays and enable their formulation into various pharmaceutical compositions (including delivery systems). In an aspect, the medicinal clay compositions are stable for a period of at least 1 year, at least 1.5 years, or at least 2 years.

In an embodiment, the medicinal clay compositions comprise at least one coating polymer that is inert and does not undergo any reaction with the medicinal clay until it contacts moisture, or a water source, at a site of use or site for treatment. Examples of suitable coatings include polymers, such as nonionic block EO-PO copolymer(s), mineral salts, pectin, chitosan, polysaccharides, such as the organic polymer maltodextrin, water soluble or hydrocolloid polymers, and the like as described herein. In preferred embodiments, the coating for the clay is at least about 1 micron to about 100 microns in thickness.

In some embodiments, the coating agent (or combinations of more than one coating agent) is included in the medicinal clay compositions at an amount of at least about 10 wt-% to about 90 wt-%, about 10 wt-% to about 80 wt-%, about 10 wt-% to about 70 wt-%, about 20 wt-% to about 80 wt-%, about 20 wt-% to about 70 wt-%, or about 30 wt-% to about 80 wt-%. In addition, without being limited according to the disclosure, all ranges recited are inclusive of the numbers defining the range and include each integer within the defined range.

Polymers

In an embodiment, the coating polymer is a nonionic block EO-PO copolymer(s) (also includes poly (ethylene oxide) (PEO)—poly (propylene oxide) (PPO) copolymers). Without being limited to a particular mechanism of action the nonionic block EO-PO copolymer(s) not only coat the clay to prevent a water source, moisture, or hydration from prematurely activating the clay, the coating polymers provide beneficial anti-pathogenic properties as they can effectively carry pharmaceutical compounds, such as additional therapeutic agents, into the pathogens and killing the pathogens. The various capabilities of the nonionic block EO-PO copolymer(s) can provide synergistic anti-pathogenic properties to the medicinal clay compositions.

The synergistic effects of the coating agent/polymer with the clay are distinct from the prior use of polymers to coat clay, such as disclosed in U.S. Pat. No. 10,105,388. The prior art has only applied inert polymers for a film, such as cellulose acetate, ethyl cellulose, methyl cellulose, hydroxypropyl methyl cellulose, polyvinyl alcohol, dextrins, starches and gums, to provide a thin film added over the clay (and binders).

In embodiments, the nonionic block EO-PO copolymers include, but are not limited to, poloxamers. These poloxamers are odorless, tasteless, white, waxy granules with free-flowing properties. Poloxamers are amphiphilic in nature, as they are soluble in both polar and nonpolar solvents. The amphiphilic properties stem from a tri-block configuration, consisting of a hydrophobic unit [poly (propylene oxide) (PPO)] in between two hydrophilic units [poly (ethylene oxide) (PEO)] with the basic sequence of A-B-A and having the structure ($PEO_a$-$PPO_b$-$PEO_a$) shown below:

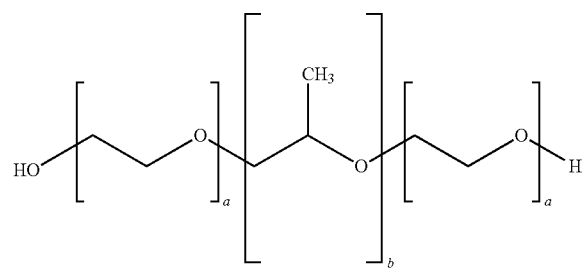

Exemplary poloxamers and the number and average size of EO/PEO and PO/PPO blocks include those shown by Chowdhury P. et al., *Pluronic Nanotechnology for Overcoming Drug Resistance*. In: Yan B. et al. (eds) Bioactivity of Engineered Nanoparticles (2017), which is reproduced below as Table 3:

TABLE 3

| Name | Average Molecular Weight (g/mol) | No. of EO units | No. of PO units |
|---|---|---|---|
| Poloxamer 124 (Pluronic ® L-44) | 2090-2360 | 12 | 20 |
| Poloxamer 188 (Pluronic ® F-68) | 7680-9510 | 80 | 27 |
| Poloxamer 237 (Pluronic ® F-87) | 6840-8830 | 64 | 37 |
| Poloxamer 338 (Pluronic ® F-108) | 12700-17400 | 141 | 44 |
| Poloxamer 407 (Pluronic ® F-127) | 9840-14600 | 101 | 56 |
| Poloxamer 401 (Pluronic ® L121) | 4400 | 10 | 68 |
| Poloxamer 184 (Pluronic ® L-64) | 2900 | 26 | 30 |

Additional exemplary poloxamers include Poloxamer 105 having a molecular structure: polymer with oxirane (11; 16) where oxirane means ethylene oxide, also described as $EO_{27}PO_{56}EO_{27}$. Further Poloxamer 85 has a molecular structure: triblock copolymer with central chain of poly (propylene oxide) (70 units) flanked by two hydrophilic chains of poly(ethylene oxide) (20 units), function: surfactant.

These EO-PO copolymers have the same chemical structure but differ in the number of EO/PEO and PO/PPO units, as well as in molecular weight. Due to the hydrophobic and hydrophilic nature of the poloxamers, the amphiphilic properties of poloxamers differ depending on the number of EO/PEO or PO/PPO units, and can be determined by the hydrophilic-lipophilic balance (HLB) of the poloxamer.

In embodiments, the nonionic block EO-PO copolymer has the formula $PEO_a$-$PPO_b$-$PEO_a$, where the sum of a=70-120 and b=40-65 and/or has the formula $PEO_a$-$PPO_b$-$PEO_a$, where the sum of a=70-100 and b=20-35.

In other embodiments, suitable polymers include a diblock polymer comprising a PEO block and a PPO block, a center block of polyoxypropylene units (PPO), and having blocks of polyoxyethylene grafted onto the polyoxypropylene unit or a center block of PEO with attached PPO blocks. Further, this polymer can have further blocks of either polyoxyethylene or polyoxypropylene in the molecules. A suitable average molecular weight range of useful surfactant polymers can be about 1,000 to about 40,000 (molecular mass) and the weight percent content of ethylene oxide can be about 20-90 wt-%. In embodiments, the nonionic EO-PO copolymer having an average molecular weight of from about 5,000 to about 20,000 and a weight percent content of ethylene oxide of from about 50-80 wt % or from about 60-90 wt-%.

In further embodiments, the nonionic block EO-PO copolymer for coating the medicinal clay is poloxamer 407 and/or poloxamer 188. Without being limited to a particular mechanism of action, the use of the nonionic block EO-PO copolymers beneficially control and enhance release of the clay when the coated clay contacts a water source (i.e., hydration or moisture). Further, the nonionic block EO-PO copolymers, in particular the poloxamer 407 is particularly effective at taking therapeutic agents—including the medicinal clay—into pathogens and killing the pathogens (i.e., "Trojan Horse" effect). Moreover, the nonionic block EO-PO copolymers, in particular the poloxamer 188 is particularly effective at cellular healing and bandaging broken membranes, also referred to as a membrane resealing reagent. According to particular embodiments, coating of the medicinal clay with the poloxamer 407 and/or poloxamer 188 provides unexpected benefits in cellular entry and membrane healing. For example, in an embodiment a first coating of the poloxamer 188 is employed and a second coating of poloxamer 407 is thereafter employed to first facilitate the entry of the coated clay into microbial cells and thereafter facilitate cellular healing.

Mineral Salts

In an embodiment, the coating agent further comprises a mineral salt or a composition of a blend of mineral salts. Exemplary mineral salts include sodium chloride, magnesium chloride, sodium sulfate, calcium chloride, potassium chloride, etc. Without being limited to a particular mechanism of action, the mineral salts replicate amniotic fluid (or other bodily fluids) to reintroduce the minerals into a wound (or other treatment location) where the medicinal clay composition is needed.

In an embodiment, mineral salts can be provided from a commercially available blend such as Instant Ocean Sea Salt Mixture, provide a mixture of sodium chloride, magnesium chloride, sodium sulfate, calcium chloride and potassium chloride. In an embodiment the coating agent comprises at least two, at least three, or at least four, or at least five mineral salts. In an embodiment the coating agent comprises at least two, at least three, or at least four, or at least five mineral salts from the group sodium chloride, magnesium chloride, sodium sulfate, calcium chloride, and potassium chloride.

In embodiments, the mineral salts are preferred as a coating agent in combination with a nonionic block EO-PO copolymer(s) in a ratio of about 1:1 to about 20:1 mass ratio of the nonionic block EO-PO copolymer(s) to the mineral salts.

Polysaccharide Polymers

In an embodiment, the coating agent is a polysaccharide polymer. The material can be an organic polysaccharide. An example of a polysaccharide is maltodextrin having the formula $C_{6n}H_{(10n+2)}O_{(5n+1)}$ where n is 2-20. In some embodiments, maltodextrin beneficially further enhances the clay delivery as the pH of maltodextrin is approximately 3 providing a beneficially acidic pH for treatment conditions for the delivery and activation of the clay.

In a further embodiment glycols and/or glycerols may be further used as coating agents/polymers. In some embodiments, it may be desirable to combine glycerin with a polysaccharide coating such as maltodextrin.

In a further embodiment water soluble or hydrocolloid polymer can be used as the coating agents/polymers. These polymers beneficially provide the medicinal clay with an ORP and pH protecting layer(s). Exemplary polymers include pectin, chitosan, alginate, hydrophilic colloids, sodium carboxymethyl cellulose, hydroxypropyl cellulose, hydroxypropyl methyl cellulose, polyvinylpyrrolidone (PVP), Arabic gum, xanthan gum, tragacanth gum, Carbopol, ethyl cellulose, cellulose acetate phthalate, and the like. Beneficially, in the various embodiments, the polymers can be organic polymers.

Additional Therapeutic Agents

Additional therapeutic agents can optionally be included in the pharmaceutical compositions. In some embodiments few or no additional therapeutic agents are disposed therein the medicinal clay compositions and/or the pharmaceutical compositions.

In embodiments including an additional therapeutic agent, these can include components conventionally intended for pharmaceutical preparations, including for example to provide antipathogenic, antibacterial, antimicrobial, biocidal, etc. therapeutic benefits, properties and/or functionalities to the compositions.

In an embodiment, the at least one additional therapeutic agent is a therapeutic cation, such as silver ($Ag^+$). The at least one additional therapeutic agent can be further incorporated into the medicinal clay composition or can be combined with the medicinal clay compositions to provide the pharmaceutical composition. In embodiments where the additional therapeutic agent is combined with the medicinal clay compositions it can also further serve as a delivery vehicle for the medicinal clay composition for delivery to the target site (e.g., tissue or organ in need of treatment).

In an embodiment, the additional therapeutic agent is a therapeutic cation, e.g., silver ($Ag^+$). Silver has antimicrobial activity takes place after the silver atoms are oxidized by water or wound fluid and the atoms become cationic. Once chloride binds to silver cations the silver is rendered insoluble, non-antimicrobial, and ineffective. Chloride is the main nutrient in wound fluid (i.e., exudate), and it is an anion that rapidly binds to cationic silver. In an embodiment with a therapeutic cation (e.g., silver) as a therapeutic agent delivered with a medicinal clay chelates chloride found in wound fluid before the chloride contacts the silver, prior to its contact with silver to mitigate the binding of silver and chloride.

Incorporating cationic silver in the medicinal clay composition as an additional therapeutic agent allows the clay to bind to anions (e.g., chloride) present in wound exudate and mitigate chelation of therapeutic cations. Such exemplary therapeutic cations can include calcium ($Ca^{2+}$), magnesium ($Mg^{2+}$), and potassium ($K^+$), sodium ($Na^+$), silver ($Ag^+$), hydrogen ($H^+$), aluminum ($Al^{3+}$), iron ($Fe^{3+}$), iron ($Fe^{2+}$), manganese ($Mn^{2+}$), zinc ($Zn^{2+}$) and copper ($Cu^{2+}$). Beneficially, the therapeutic cations survive contact with the wound exudate as a result of the medicinal clay binding to the chloride in the wound fluid.

Biofilm inhibiting coatings can also be included as additional therapeutic agents. As biofilms are present in most chronic wounds and present a significant obstacle to both wound healing and penetration of antipathogenic agents. Products that are able to disrupt biofilms and inhibit biofilm formation without harming healthy surrounding tissues are vital to adequately address pathogenic bioburden and promote wound healing can be included in the compositions described herein. Clay compositions can incorporate a variety of non-cytotoxic coatings (e.g., chitosan, poloxamers, and pectin), and allow for improved penetration of the antimicrobial reduced cations provided from the medicinal clay. In some embodiments, the therapeutic agent for disrupting and inhibiting biofilm can be included in the compositions in an amount from about 0.0001-1 wt-%, or from about 0.001-1 wt-%, or from about 0.01-1 wt-%.

Beneficially, the therapeutic agent is a non-cytotoxic component. In some embodiments, the therapeutic agent does not include cationic antimicrobials, such as quaternary ammonium salts, alkyl pyridinium salts, alkyl imidazolium salts, alkyl morpholinium salts, benzethonium salts, ethoxylated quaternary ammonium salts, or the like, as disclosed in U.S. Pat. No. 9,675,077. Such exemplary cationic antimicrobials, namely benzalkonium, benzethonium, dimethyldialkylonium, alkylpyridinium and alkyltrimethylammonium cations act in a non-discrete and cytotoxic manner as they are potent and fast-acting cytotoxins. Benzalkonium chloride is a well-known cationic antimicrobial that is both cytotoxic and known to denature proteins. Such examples of cationic antimicrobials are not included in the compositions and methods described herein as they are unwanted and detrimental to treating subjects, namely wound beds and wound tissue.

According to additional embodiments of the disclosure, the various additional therapeutic agents may be provided in the pharmaceutical compositions in the amount from about 0 wt-% and about 90 wt-%, from about 0.00001 wt-% and about 80 wt-%, from about 0.0001 wt-% and about 70 wt-%, from about 0.0001 wt-% and about 60 wt-%, from about 0.001 wt-% and about 50 wt-%, from about 0.001 wt-% and about 40 wt-%, from about 0.001 wt-% and about 30 wt-%, from about 0.01 wt-% and about 25 wt-%, from about 0.1 wt-% and about 50 wt-%, from about 0.1 wt-% and about 25 wt-%, from about 1 wt-% and about 50 wt-%, from about 1 wt-% and about 25 wt-%, from about 10 wt-% and about 50 wt-%, or from about 10 wt-% and about 25 wt-%. In addition, without being limited according to the disclosure, all ranges recited are inclusive of the numbers defining the range and include each integer within the defined range.

Additional Functional Ingredients

Additional functional ingredients can optionally be included in the medicinal clay compositions and/or the pharmaceutical compositions. In some embodiments few or no additional functional ingredients agents are disposed therein the medicinal clay compositions and/or the pharmaceutical compositions.

In embodiments including an additional functional ingredient, these can include components conventionally included with pharmaceutical preparations, including for example preparations for topical administration. Examples that may be mentioned are additives which are suitable for producing a desired delivery or dosage form, such as film, electro-spun materials, foam, hydrocolloid, hydrogel, gel, alginate gel, gel sheet, emulsion, suspension, paste, cream, ointment, cream, powder, tablet, capsule, transdermal therapeutic system or dressing or other delivery system impregnated with the medicinal clay composition. The functional ingredients provide desired properties and functionalities to the compositions, including a material that when combined with a therapeutic agent provides a beneficial property in a particular use or treatment. In certain embodiments, the compositions can include a solvent as an additional functional ingredient. Suitable solvents include, but are not limited to, water, glycols and glycerins, rosemary, *eucalyptus*, ethanol, butylene glycol, propylene glycol, propanediol, isopropyl alcohol, isoprene glycol, glycerin, Carbowax (polyethylene glycol) 200, Carbowax 400, Carbowax 600, and Carbowax 800. In addition, combinations or mixtures of these solvents may be used according to the present disclosure. In one particular embodiment, the solvent is water.

Suitable viscosity adjusting agents (i.e., thickening and thinning agents) as an additional functional ingredient for the compositions include, but are not limited to, protective colloids or non-ionic gums such as pectin, chitosan, glucans, carrageenan, hydroxyethylcellulose (e.g., Cellosize HEC QP52,000-H, manufactured by Amerchol), xanthan gum, and *sclerotium* gum (Amigel 1.0), as well as magnesium aluminum silicate (Veegum Ultra), silica, microcrystalline wax, beeswax, paraffin, petrolatum, and cetyl palmitate. In addition, appropriate combinations or mixtures of these viscosity adjusters may be utilized.

Suitable surfactants as an additional functional ingredient for use in the compositions include, but are not limited to, additional nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-diimonium chloride). Combinations of surfactants may also be employed.

The compositions may also include one or more preservatives as an additional functional ingredient. Suitable preservatives include, but are not limited to, anti-microbials such as Lincoserve BDP, Germaben II (manufactured by ICI; propylene glycol, diazolidinyl urea, methylparaben, and propylparaben), Net-DTB (Isopropyl-methyl phenol), methylparaben, propylparaben, imidazolidinyl urea, benzyl alcohol, sorbic acid, benzoic acid, sodium benzoate, dichlorobenzyl alcohol, phenoxyethanol, dehydroacetic acid, and formaldehyde, as well as physical stabilizers and anti-oxidants such as alpha-tocopherol (vitamin E), sodium ascorbate/ascorbic acid, ascorbyl palmitate and propyl gallate. In addition, combinations or mixtures of these preservatives may also be used.

Various additives, known to those skilled in the art, may also be included in the compositions including those disclosed in U.S. Pat. No. 9,095,542, which is herein incorporated by reference in its entirety. In certain embodiments, for example, it may be desirable to include one or more skin permeation enhancers as an additional functional ingredient in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184, P85, P105, P338), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, and diethanolamine; terpenes; alkanones; and organic acids, particularly citric acid and succinic acid. Azone® and sulfoxides such as DMSO and C10 MSO may also be used.

Other enhancers are those lipophilic co-enhancers typically referred to as "plasticizing" enhancers, i.e., enhancers that have a molecular weight in the range of about 150 to 1000, and an aqueous solubility of less than about 1 wt. %. Lipophilic enhancers include fatty esters, fatty alcohols, and fatty ethers. Examples of specific fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, e.g., a C2-C4 alkane diol or triol, is substituted with one or two fatty ether substituents.

Additional permeation enhancers will be known to those of ordinary skill in the art of drug delivery, and/or are described in the pertinent texts and literature. See, e.g., Percutaneous Penetration Enhancers, eds. Smith et al. (CRC Press, 1995).

The compositions may also comprise one or more moisturizers as an additional functional ingredient. Suitable moisturizers for use in the formulations of the present disclosure include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations described herein include, but are not limited to, PPG-15 stearyl ether, lanolin alcohol, lanolin, lanolin derivatives, cholesterol, propanediol, isostearyl neopentanoate, octyl stearate, mineral oil and various other oils, such as rosemary, olive oil, argon and *eucalyptus*, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors as an additional functional ingredient, such as FD&C Red No. 40 and FD&C Yellow No. 5, and natural colorants (e.g., vivianite) may also be used in the formulations.

Other suitable ingredients which may be included in the compositions include, but are not limited to, abrasives, absorbents, anti-caking agents, anti-foaming agents, anti-static agents, astringents (e.g., witch hazel, alcohol, and herbal extracts such as chamomile extract), binders/excipients (e.g., starches, tragacanth, celluloses, such as cellulose ethers including methyl cellulose or hydroxypropyl methyl cellulose), buffering agents, film forming agents, conditioning agents, opacifying agents, pH adjusters (e.g., citric acid and sodium hydroxide), osmotic modifiers (e.g., marine salts, sodium chloride, and potassium chloride), and protectants. Examples of each of these ingredients, as well as examples of other suitable ingredients in product formulations, may be found in publications by The Cosmetic, Toiletry, and Fragrance Association (CTFA). See, e.g., CTFA Cosmetic Ingredient Handbook, 2$^{nd}$ edition, eds. John A. Wenninger and G. N. McEwen, Jr. (CTFA, 1992).

The compositions may also contain irritation-mitigating additives to minimize or eliminate the possibility of skin irritation or skin damage resulting from the pharmacologically active base or other components of the composition. Suitable irritation-mitigating additives include, for example: beta glucan, glucans, alpha-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; cis-urocanic acid; capsaicin; L-sulforaphane; Curcumin; and chloroquine. The irritant-mitigating additive, if present, may be incorporated into the present compositions at a concentration effective to mitigate irritation or skin damage.

These additional components can be formulated into the medicinal clay compositions and/or the pharmaceutical compositions. One skilled in the art will ascertain that the final formulation will determine additional agents needed for a particular vehicle of delivery form.

According to embodiments of the disclosure, the various additional functional ingredients may be provided in a medicinal clay composition in the amount from about 0 wt-% and about 70 wt-%, from about 0 wt-% and about 60 wt-%, from about 0 wt-% and about 50 wt-%, from about 0 wt-% and about 40 wt-%, from about 0 wt-% and about 30 wt-%, from about 0 wt-% and about 25 wt-%, from about 0.1 wt-% and about 70 wt-%, from about 0.1 wt-% and about 60 wt-%, from about 0.1 wt-% and about 50 wt-%, from about 0.1 wt-% and about 40 wt-%, from about 0.1 wt-% and about 30 wt-%, from about 0.1 wt-% and about 25 wt-%, from about 1 wt-% and about 50 wt-%, or from about 1 wt-% and about 25 wt-%. In addition, without being limited according to the disclosure, all ranges recited are inclusive of the numbers defining the range and include each integer within the defined range.

According to additional embodiments of the disclosure, the various additional functional ingredients may be provided in the pharmaceutical compositions in the amount from about 0 wt-% and about 90 wt-%, from about 0 wt-% and about 80 wt-%, from about 0 wt-% and about 70 wt-%, from about 0 wt-% and about 60 wt-%, from about 0 wt-% and about 50 wt-%, from about 0 wt-% and about 40 wt-%, from about 0 wt-% and about 30 wt-%, from about 0 wt-% and about 25 wt-%, from about 0.1 wt-% and about 50 wt-%, from about 0.1 wt-% and about 25 wt-%, from about 1 wt-% and about 50 wt-%, from about 1 wt-% and about 25 wt-%, from about 10 wt-% and about 50 wt-%, or from about 10 wt-% and about 25 wt-%. In addition, without being limited according to the disclosure, all ranges recited are inclusive of the numbers defining the range and include each integer within the defined range.

EXEMPLARY EMBODIMENTS

The medicinal clay compositions and pharmaceutical compositions can include multiple layers or coatings of desired thickness. The layers or coatings can include either a single or more than one layer of medicinal clay, as well as one or more layers of the coating agent, and other additional functional and/or therapeutic agents. An exemplary depiction of a composition with a medicinal clay is shown in FIG. 1, wherein the composition 10 has a single layer of medicinal clay (e.g., Fentonite™) 12 that is coated with a layer of the coating agent 18 (and can further include a buffer 14 and/or therapeutic agent 16 in combination with the coating agent or as further outer layer although not depicted).

Figure 2:
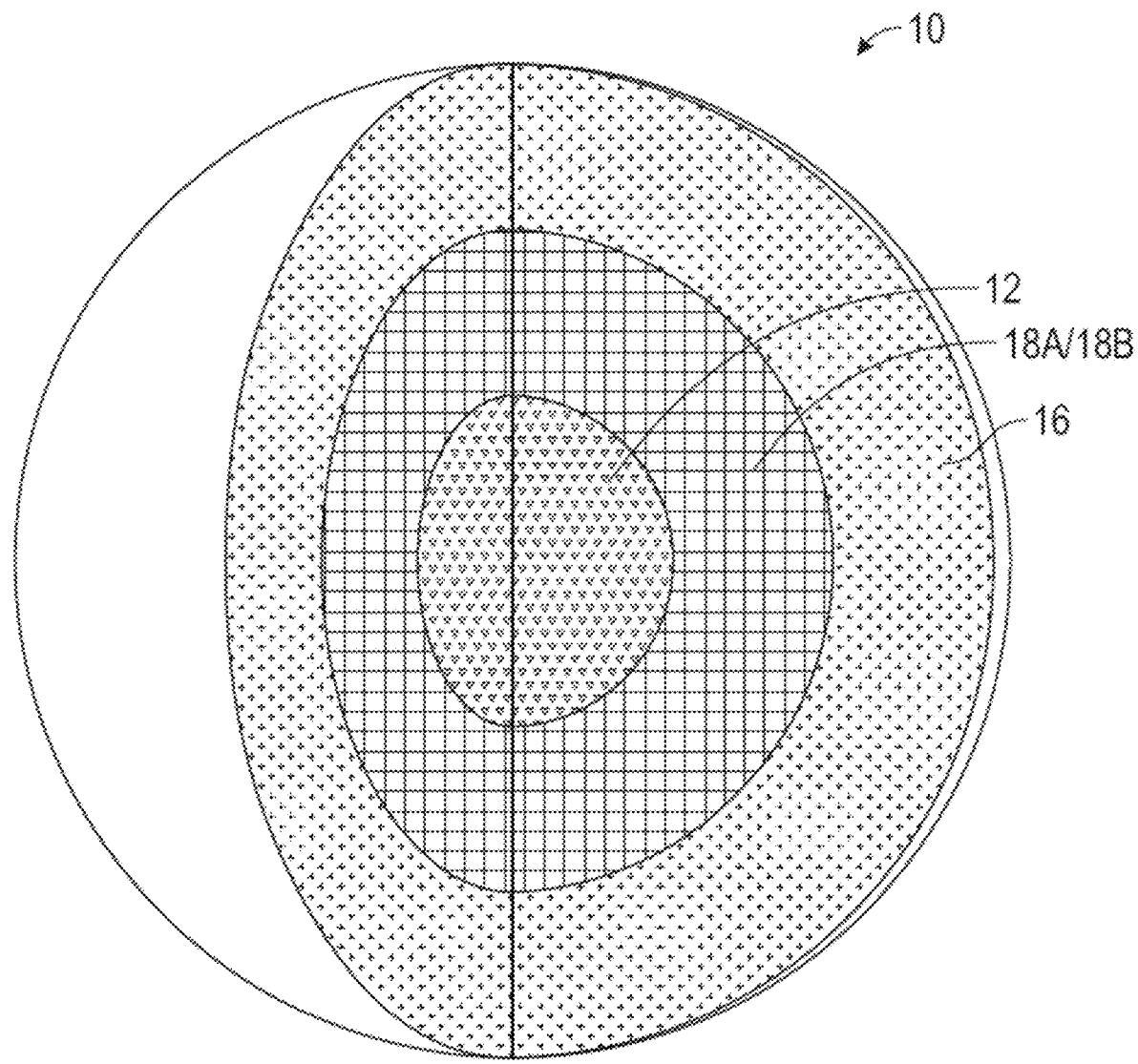

A further exemplary depiction of a composition with a medicinal clay is shown in FIG. 2, wherein the composition 10 has a single layer of medicinal clay (e.g., Fentonite™) 12 that is coated with a layer that is a blend of more than one coating agent (e.g., mineral salts and poloxamer(s)) 18A/18B, and an outer layer of the therapeutic agent 16.

Figure 3:
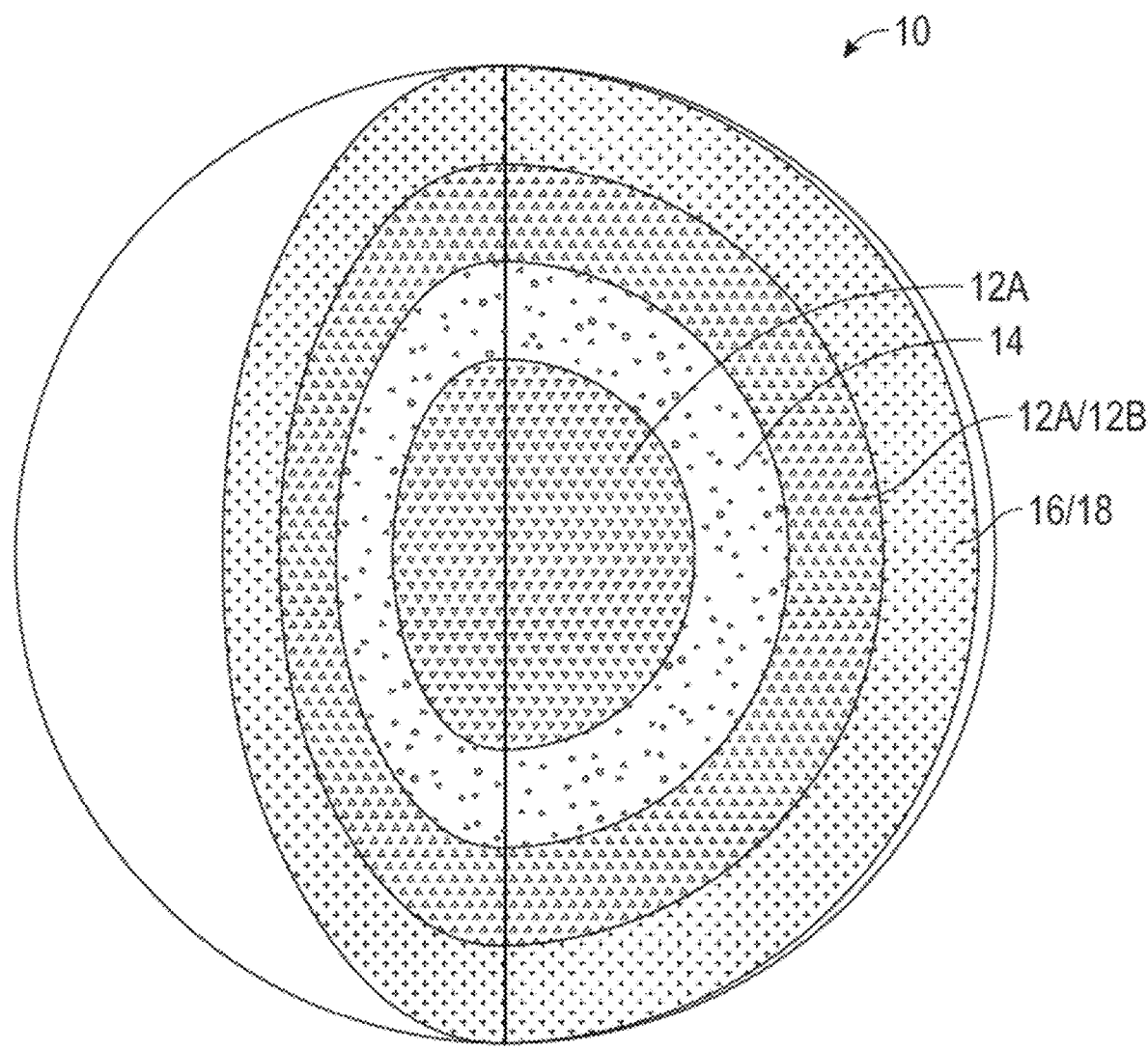

In additional embodiments, the layers or coatings can include more than one layer of medicinal clay, more than one layer of the coating agent, and other additional functional and/or therapeutic agents. An exemplary depiction of a pharmaceutical composition with a medicinal clay is shown in FIG. 3, wherein the composition 10 has two layers of medicinal clay (e.g., Fentonite™) 12A/12B, wherein the medicinal clay can include different particle sizes of the clay in each layer. In the depicted embodiment, the medicinal clay 12 can include a first particle size 12A (e.g., <100μ) and a second particular size 12B (e.g., <25μ). However, in other embodiments the same particle size could be used in a single composition 12A/12A. The composition of FIG. 3 includes a layer of buffer 14 between the medicinal clay 12A/12A (or 12/B) and an outer layer of the coating agent 18 and therapeutic agent 16 (e.g., silver, etc.).

Figure 4:
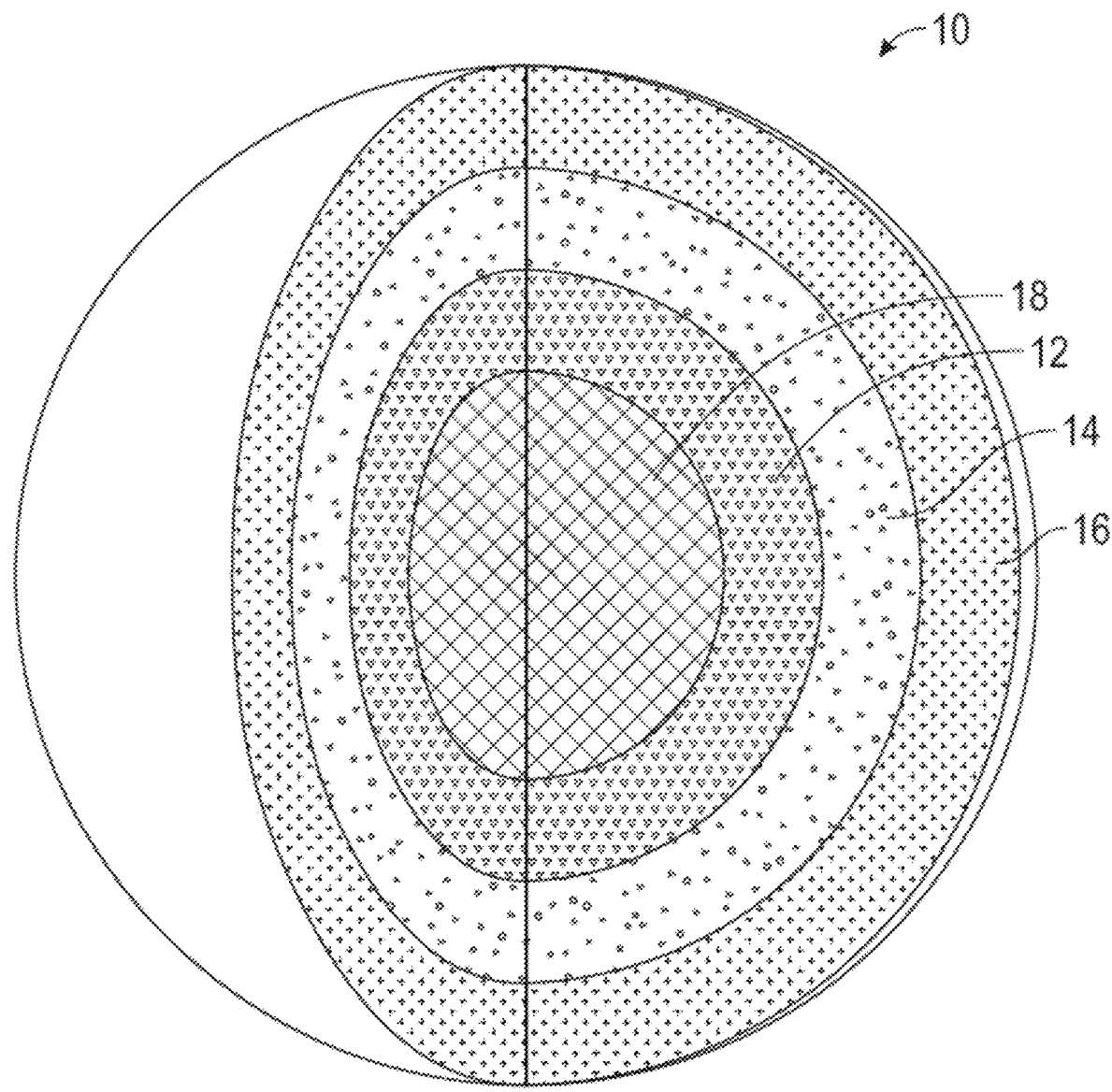

Another exemplary depiction of a medicinal clay composition is shown in FIG. 4, wherein the composition 10 has an inner core of a coating agent 18 (e.g., polymer), a single layer of medicinal clay 12 (e.g., <100μ), a buffer 14, and an outer layer of the therapeutic agent 16.

Figure 5:
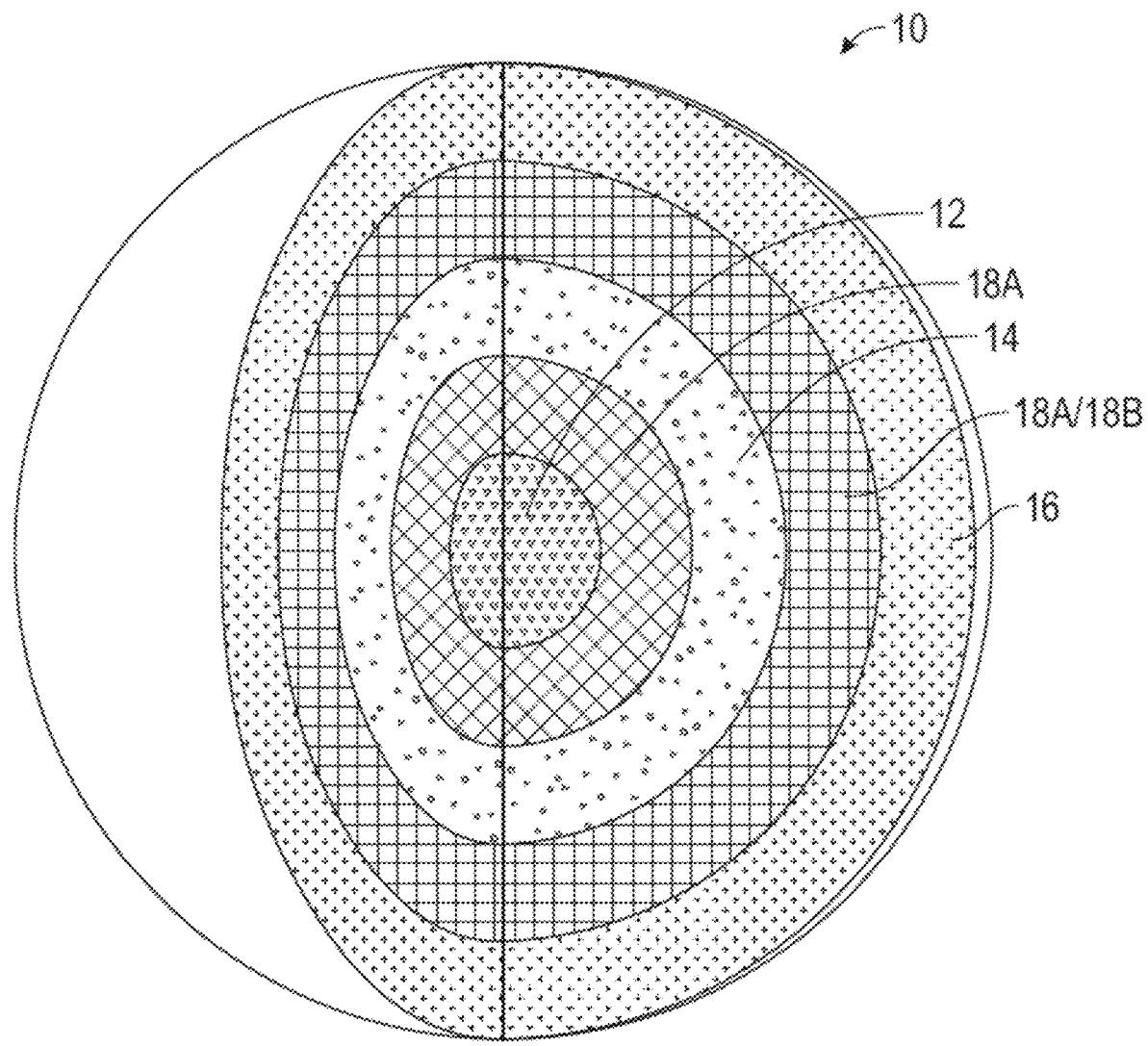

Another exemplary depiction of a pharmaceutical composition with a medicinal clay is shown in FIG. 5, wherein the composition 10 has an inner core of a single layer of medicinal clay 12 (e.g., <100μ), a first coating agent 18A (e.g., polymer 1), a buffer 14, a second coating agent 18B (e.g., polymer 2), and an outer layer of the coating agent and therapeutic agent 16 (e.g., silver, etc.). In this depicted embodiment two different polymers are employed. In embodiments a single polymer could be used for each layer and instead have different thickness (for example as shown the outer layer of coating agent shows 18A/18B, indicating it could be the same 18A coating agent and/or a combination with or a different coating agent 18B).

In each of exemplary embodiments depicted varying layers or coatings can have desired thickness. Moreover, any buffers, coatings, binders and/or therapeutic agents as described herein can be employed. It is beneficially that in many embodiments multiple layers are included to beneficially provide the coated medicinal clay in a delivery system that survives manufacturing and delivery through bodily fluids to provide the medicinal clay to a point of us.

Methods of Making Medicinal Clay Compositions and Pharmaceutical Compositions

The methods of making medicinal clay compositions include the steps of applying a coating to a clay surface to produce a medicinal clay composition, wherein the clay is a medicinal natural clay or clay mineral, a synthetic clay or clay mineral, or combinations thereof, having at least two of the following product specifications: a Cation Exchange Capacity of at least about greater than about 10 mEq/100 g, an Oxidation-Reduction Potential greater than about 250 mV, a pH less than about 5.0, a clay crystalline composition of smectite, illite, and/or illite-smectite that is at least about 40 wt-% of the clay, and/or less than 40 ppm heavy metal contaminants.

According to embodiments the coating is a coating agent comprising a nonionic block EO-PO copolymer, polysaccharide, water soluble or hydrocolloid polymer, mineral salt, or combination thereof. In embodiments the clay comprises at least about 20 wt-% of the medicinal clay composition, and the coating agent surrounding the clay has a thickness of at least about 40 microns. Beneficially, the coating process retains the Cation Exchange Capacity, Oxidation-Reduction Potential and pH of the clay. The clay specifications for medical clays as described herein can be coated using these processes for coating or encapsulating. The coating agent as described herein can be used for the processes for coating or encapsulating. In preferred embodiments the coating agent is atomized to allow the coating with a single or multiple core-shell structures.

In one embodiment, the coating or encapsulating process for coating the clay with the coating agent employs fluid bed microencapsulation. As referred to herein fluid bed microencapsulation can include Wurster processes, such as using differential air streams that move the particulates as they are coated. In embodiments, the differential air streams move the particulates upward in a cyclic motion as it is coated with the coating agent. In embodiments the coating agent is an atomized material to create a single or multiple core-shell structure. The process coats individual particles to a desired thickness and controls or prevents agglomeration. Each coating (e.g., microencapsulation with a fluid bed microencapsulation process) can vary in its precise thickness, creating unique layers and time release points.

In embodiments the coating of the clay with the coating agent employs a fluidizing solvent (e.g., methanol) that is volatized off (e.g., within a few minutes) ensuring that clay is not at risk of hydration. Additional exemplary solvents include ethanol, methanol, cyclohexane, ethylene glycol, dichloromethane, etc.

In another embodiment, the coating process employs an electrospinning technique to coat or more specifically microencapsulate clay particles into a linear or non-linear nanofiber system with or without a buffering system. Electrospinning produces fibers via an electric force which melts the fiber material into a nanofiber. In embodiments, the electrospinning process embeds the clay within the electrospun fibers, so the clay particles are surrounded by material. The electro-spun nanofiber material may be comprised of or incorporate previously described polymers, polysaccharides, and/or additional functional ingredients (e.g., pectin, chitosan, alginates, hydrophilic colloids, sodium carboxymethyl cellulose, hydroxypropyl cellulose, hydroxypropyl methyl cellulose, Arabic gum, xanthan gum, tragacanth gum, Carbopol, ethyl cellulose, cellulose acetate phthalate, and the like). The types and combinations of coating agents used may be adjusted to achieve specific time-release characteristics for the medicinal clay composition.

In another embodiment, the coating process microencapsulates the clay material into films (e.g., layers of material) or sheets that may be comprised of or incorporate previously described buffers, polymers, polysaccharides, and/or additional functional ingredients (e.g., pectin, chitosan, alginates, hydrophilic colloids, sodium carboxymethyl cellulose, hydroxypropyl cellulose, hydroxypropyl methyl cellulose, Arabic gum, xanthan gum, tragacanth gum, Carbopol, ethyl cellulose, cellulose acetate phthalate, and the like). In embodiments, the microencapsulation into films or sheets surrounds the clay by the film/sheet material, for example, clay and pectin can be mixed, hydrated, and thereafter dehydrated to form a film where the clay is microencapsulated (e.g., surrounded) by the pectin material. The types and combinations of coating agents used may be adjusted to achieve specific time-release characteristics for the microencapsulated clay. In one embodiment, the microencapsulation materials are not mixed or hydrated in a fluid bed of water or other solvent. As a result, slurries are not part of the coating process. The clay particles are not extruded or rescreened for particle size. Each particle that is coated is of a precise micron size regardless of the number of layers are added.

The methods of coating or encapsulating of the clay ensure that the coating process provides ORP, CEC, and pH of the medicinal clay within set specifications, defined herein, to assure anti-pathogenic activity remains within viable ranges. In an embodiment the coated medicinal clay retains a Cation Exchange Capacity of at least about greater than about 10 mEq/100 g, an Oxidation-Reduction Potential greater than about 250 mV, and a pH less than about 5.0. In embodiments the coated clay may be modified by a functional ingredient and/or therapeutic agent, however the modification maintains a Cation Exchange Capacity of at least about greater than about 10 mEq/100 g, an Oxidation-Reduction Potential greater than about 250 mV, and a pH less than about 5.0.

A further step of sterilizing a medicinal clay before or after coating or encapsulating can optionally be employed depending on the intended application. Sterilization methods should be validated to ensure effective sterilization without negatively impacting product stability or anti-pathogenic activity measures of the coated or encapsulated clay material.

The medicinal clay composition can be provided in various forms, including flowable powders, granules, tablets, or the like, depending upon the size of the clay that is coated and the thickness of coating agent applied thereon. Powders refer to a solid composed of a mixture of dry, finely divided active and/or inert ingredient(s). Capsules refer to solids contained within either a hard or soft soluble shell, usually prepared from gelatin. Tablets refer to solids composed of a mixture of active and/or inert ingredient(s) are pressed or compacted together. In some embodiments no further processing is required for application or administration of the medicinal clay compositions to a subject in need of treatment. For example, in some embodiments, the medicinal clay compositions are suitable for oral or topical administration.

In other embodiments, further processing can take place to provide the medicinal clay in a desired delivery system or pharmaceutical composition. In these embodiments, the medicinal clay compositions can be further combined with the additional therapeutic agents and/or additional functional ingredients. In still further embodiments the medicinal clay compositions can be impregnated into a delivery system, such as a film, foam, hydrocolloid, hydrogel, dressing, bandage, or the like. Foam formulations refer to aerated solutions or suspensions containing a dispersion of one or more liquid and/or solid ingredients. In embodiment, foams include for example, aerogels, and the like. Hydrocolloid formulations refer to hydrophilic polymers, which are dispersed in a substance and form stable colloids in water. In embodiments, hydrocolloids include for example, xanthan gum, guar gum, locust bean gum, gum Arabic, cellulose derivatives, starch, and the like. Gel formulations refer to semi-solids composed of a solid, three dimensional (3D) cross linked matrix of polymers within a liquid, yielding a jelly-like material unable to flow at a steady state. In embodiments, gels include for example, agar, hydrogels, alginate gels, gel sheets, and the like. Emulsions refer to semi-solids composed of at least two immiscible liquids, one of which is dispersed as droplets within the other liquid and is stabilized with one or more emulsifying agents. In embodiments, emulsions include for example, creams, ointments, and the like. A cream refers to a semi-solid composed of an emulsion of lipids, hydrocarbons, waxes, or polyols in water. An ointment refers to a semi-solid that may be composed of a variety of bases including hydrocarbons, emulsifiers or vegetable oils, and mixed with active and/or inert ingredient(s). Suspensions refer to insoluble solid particles composed of active and/or inert ingredient(s), which are sufficiently large for sedimentation, are dispersed in a liquid. In embodiments, suspensions include for example, pastes, and the like. A paste refers to a semi-solid composed of a large proportion of solids and finely dispersed active and/or inert ingredient(s) in a fat-based vehicle.

In an exemplary embodiment, a medicinal clay composition is provided as an additive to a foam and/or hydrocolloid dressing. A dressing refers to a substance intended for administration in or on a wound. In embodiments, dressings include for example, gauze, foam, hydrocolloids, gels, pads, and the like. Beneficially, the medicinal clay composition is protected from further processing (i.e., secondary manufacturing) required to provide various delivery or dosing applications, namely those that contain water or aqueous environments.

Methods of Treatment Using a Medicinal Clay Composition or Pharmaceutical Compositions Methods for treatment using the medicinal clay compositions or pharmaceutical compositions include a step of applying the composition to a subject, namely a tissue or organ in need of treatment. The step of applying can include coating a site with a topical application of the pharmaceutical composition or medicinal clay composition. Such topical applications can include for example applying a paste, cream, ointment, foam, hydrocolloid, hydrogel, gel, or the like. The step of applying can also include oral administration, intestinal track, rectal or vaginal administration, such as applying a flowable powder, tablet, capsule, gel, suppository, suspension, dressing or other delivery system.

The methods of treatment are highly effective as the medicinal clay, as a cation source, is applied to a tissue or organ in need of treatment and beneficially kills pathogen cells while also being non-cytotoxic, and disrupting, preventing, inhibiting and removing biofilms, secretions, toxins and contaminants from the site (e.g., wound tissue or organ that is infected and in need of treatment). Without being limited to a particular mechanism of action, the medicinal clays have adsorption (i.e., attraction of molecules) and absorption (i.e., liquid uptake) qualities. The small particle size (e.g., preferably less than about 250, or preferably less than about 100 microns in diameter) allows for the removal of secretions, toxins and contaminants from the site. For example, bodily fluids like oils, exudate, secretions, toxins, and other contaminants can be removed by the clay absorbing these exudates.

When the clay is hydrated, or once the clay comes in contact with a water source (such as a damp wound or wound exudate as a site of treatment), the clay, as a cation source, releases solubilized cations. The cations instantly (e.g., within less than about 30 seconds, within less than about 10 seconds, or within less than about 5 seconds) seek to bind with anions, like chloride, in the water source. For example, the water source can be a wound exudate, which contains chloride that can bind and impede efficacy of therapeutic cations. When the solubilized cations of the cation source (e.g., clay) bind to anions, the action preserves any therapeutic cations in the pharmaceutical composition and allows them to retain therapeutic efficacy. Such therapeutic cations include silver (Ag+), and such solubilized cations include iron (particularly reduced $Fe^+$ and $Fe^{2+}$) and aluminum (particularly $Al^{3+}$). Beneficially, the solubilized cations damage pathogen membranes, allowing for the excess cations to cause intracellular protein damage through oxidation. Hydroxyl radicals are generated as $Fe^{2+}/Fe^{3+}/Al^{3+}$ are oxidized by $H_2O_2$ through the Fenton reaction. The proximity of .OH generation to target to be treated (i.e., tissue or organ) is important for toxicity of the pathogen as the radical .OH has a short half-life (estimated at between $10^{-9}$ second half life and also diffuses only nanometers before reacting. In an embodiment, cations, including iron (particularly reduced $Fe^+$ and $Fe^{2+}$) and aluminum (particularly $Al^{3+}$) are provided separate from the medicinal clay. Additionally, the oxidation of the therapeutic cations allows for improved efficacy of the therapeutic cations (e.g., Ag+), compounding the eradication of pathogens at the site of treatment.

There can also beneficially be remineralization of the tissue or organ of the subject that is treated with the compositions when a mineral salt is included in the coating agents. This beneficially remineralizes wounds as well as contributing to the pathogenic activity of the medicinal clay, both in a non-cytotoxic manner.

Beneficially, the anti-pathogenic activity of the clay is not activated until the clay is hydrated, or once it comes into contact with moisture, or a water source, such as upon contacting a tissue or organ of a subject in need of treatment. Once the clay is activated, the anti-pathogenic activity of the clay lasts for a period of at least about 12 hours, and more preferably, for a period of around 7 days. In embodiments, the methods provide benefits to hospitals and long-term care facilities for only requiring wound care or dressing changes daily. However, in some embodiments where pathogen infections are known to replicate more quickly, more frequent dosing may be preferred. In an exemplary embodiment, when treating MRSA, for example, dosing may be more frequently for an improved kill rate, such as two to four times daily. This will be important to ensure there is a minimum of a 2 Log pathogen reduction.

A benefit of the medicinal clay compositions (and pharmaceutical compositions containing the same) is that in some embodiments the coating itself further aids in the "Trojan Horse" attack against pathogens in need of treatment. For example, since pathogen cells are known to be aggressive in consuming concentrations of metabolites (in comparison to healthy cells) certain coatings can be attractive to the cells, such as polysaccharides or the poloxamer polymers described herein. For example, in some embodiments the nonionic block EO-PO copolymers beneficially serve as a delivery vehicle for the compositions and provide various benefits. In particular, when the temperature rises and reaches the critical micelle temperature (CMT) of the nonionic block EO-PO copolymer(s), the copolymers aggregate, forming spherical micelles, with the hydrated PEO units aligning along the outer lining, and the hydrophobic PPO units in the inner core of the micelle. The hydrophobic core of the micelles provides benefits in delivering hydrophobic drugs and other therapeutic agents. Further, in some aspects, the nonionic block EO-PO copolymers are able to prevent or have a reversal effect on multiple drug resistance (MDR) (the ability of microbes to grow even in the presence of chemicals, i.e., therapeutic agents, that would usually inhibit their growth). The nonionic block EO-PO copolymers interact with MDR cells through several different mechanisms, such as those discussed in Chowdhury P. et al., *Pluronic Nanotechnology for Overcoming Drug Resistance.*

In: Yan B. et al. (eds) Bioactivity of Engineered Nanoparticles (2017), which is hereby incorporated by reference in its entirety.

Beneficially, the clay also delivers minerals into surrounding healthy tissues and further promotes healing. For example, it is envisioned that topical application of compositions to stomas (i.e., any opening in the skin with exposed mucosal membrane) would benefit from preventative measures to maintain healthy tissues. Such topical application could be in the form of a paste, such as a hydrocolloid paste, to prevent stoma leakage onto surrounding healthy tissue. As a further benefit, in embodiments where a wet stoma is involved the medicinal clay compositions beneficially dries (through absorbing fluids) and wicks away moisture to keep off the healthy skin.

The methods described herein deliver therapeutic agents to a subject. According to additional embodiments of the disclosure, the therapeutic agent may be provided in the medicinal clay compositions or the pharmaceutical compositions in the amount from about 0 wt-% and about 90 wt-%, from about 0.0001 wt-% and about 90 wt-%, from about 0.0001 wt-% and about 70 wt-%, from about 0.0001 wt-% and about 60 wt-%, from about 0.0001 wt-% and about 50 wt-%, from about 0.001 wt-% and about 40 wt-%, from about 0.001 wt-% and about 30 wt-%, from about 0.01 wt-% and about 25 wt-%, from about 0.1 wt-% and about 50 wt-%, from about 0.1 wt-% and about 25 wt-%, from about 1 wt-% and about 50 wt-%, from about 1 wt-% and about 25 wt-%, from about 10 wt-% and about 50 wt-%, or from about 10 wt-% and about 25 wt-%. In addition, without being limited according to the disclosure, all ranges recited are inclusive of the numbers defining the range and include each integer within the defined range.

The methods described herein preferably employ the medicinal clay compositions for topical application. The medicinal clay compositions are preferably applied to the surface of a tissue or organ of the body, such as the skin, mucosal cells and tissues (e.g., alveolar, buccal, lingual, masticatory, or nasal mucosa, and other tissues and cells that line hollow organs or body cavities) or exposed tissue. In an embodiment, the methods described herein preferably employ medicinal clay compositions for application to skin, mucosal cells, intestinal track, ear canal, nasal passages, oral cavities or combinations thereof. The application beneficially prevents the breakdown of skin. Various applications can include use in diapers, underpads for bedding (e.g., for incontinency), hospital drapes, acne, and other applications of skin and wound care.

The compositions and methods of the present disclosure may be used to treat skin that is dry, cracked, itchy, scaly, or exhibiting redness or edema but otherwise appears intact to the unaided eye. Still further the compositions and methods can be used to treat areas in need of peri-wound treatment, such as where nutrients are not otherwise available (e.g., shingles, herpes, hives, poison ivy, and the like), general anti-inflammatory, anti-itch, calming and/or odor control, and the like.

The compositions and methods may also be used to treat more serious wounds, that is, wounds characterized by a partial or total thickness skin loss, including wounds that are at risk of necrosis. When a wound is characterized by a partial or total thickness skin loss, one of the phases of wound healing is the proliferative phase. The proliferative phase typically includes angiogenesis, collagen deposition, granulation tissue formation, epithelialization, and wound contraction. Wound closure thus requires that cells be in a proliferative phase and it is preferred, therefore, that any composition applied to an open wound not induce the cells in the open wound area into a quiescent state.

In still another embodiment, the compositions and methods are effective against gastrointestinal pathogens, notably *C. Difficile*. Without being limited to a particular mechanism of action, the clay delivery systems coat a treated surface (such as a tissue or organ of the body) and effectively kill the gastrointestinal pathogens, such as *C Difficile*. The coating or encapsulating provides a local effect on the gastric mucosa, coating it and protecting it from the corrosive effects of acid and pepsin while providing the local anti-pathogenic properties. *C. Difficile* burdens the health care system with costs of $3.2 billion dollars annually. It is a leading cause of hospital associated gastrointestinal illness and it places the lives of immune compromised patients and the elderly at a higher risk of complications that could lead to death. The current treatment recommendation for patients with mild to moderate *C. Difficile* is metronidazole 500 mg orally three times a day for 10 days. For patients with severe *C. Difficile*, the recommended treatment is vancomycin, 125 mg orally four times a day for 10 days. The risks associated with these recommendations are that often the *C. Difficile* was antibiotic induced. The rates of *C. Difficile* have been rising steadily since 2000. This is especially the case with the elderly confined to hospitals and long-term care facilities. Within this population the risk of *C. Difficile* could be as high as 50%. The two biggest risk factors are exposure to antibiotics and organisms common within the institutional setting. To reduce the risk of *C. Difficile* infection in patient populations the use of the clay delivery systems are administered, including for example, delivery as a syrup prophylactically or at the time of diagnosis through the course of treatment. Beneficially, such treatment provides a low cost method to protect patients and reduce the risks and complications inherent with the infection.

In various applications of using the medicinal clay compositions the clay is delivered for topical applications, in particular for anti-pathogenic treatment and/or prevention. In an embodiment, the medicinal clay compositions provide a vehicle for treating microbial infections, including chronic and non-chronic wounds in need of antimicrobial treatment. In a further embodiment, the medicinal clay compositions are particularly well suited for treating wounds with an antibiotic resistant pathogen.

In a further embodiment, the medicinal clay compositions are particularly well suited for treating biofilms commonly found in chronic wound beds and other tissues. In such embodiments, biofilms are found in wound beds, and according to some estimates are present in at least 70% of wound beds. The medicinal clay compositions disrupt, prevent, inhibit and/or remove biofilms, which means that wound biofilms are treated (including secretions, toxins and contaminants from the site) and further wound biofilm reconstitution is inhibited. Biofilm disruption, or inhibition of biofilm reconstitution, as referred to herein, refers to the ability of the clay compositions when delivered to a wound to be able to remove biofilm from a biofilm-containing chronic or acute wound, as well as inhibit reconstitution of biofilm from remnants thereof that may remain after treatment, debridement, or the like. The methods of treating biofilm-containing wounds with the medicinal clay compositions effectively promote healing of such wound which are known to contain multiple different types of bacteria, both Gram positive and Gram negative, within the biofilm that can be difficult to culture as they are clustered within a multicellular matrix-enclosed within the biofilm.

The efficacy according to the methods is effective against a broad range of pathogens, including gram positive and gram negative bacteria. Exemplary pathogens include for example, *Bacillus* spp., *Clostridium* spp. (including *C. Difficile*), *Chlamydia* spp., *Escherichia* spp., *Staphylococcus* spp., *Klebsiella* spp., *Enterococcus* spp., *Acinetobacter* spp., *Pseudomonas* spp., *Streptococcus* spp., *Bordetella* spp., *Borrelia* spp., *Campylobacter* spp., *Brucella* spp., *Mycobacterium* spp., *Salmonella* spp., *Staphylococcus* spp., including for example *Escherichia Coli, Staphylococcus aureus*, methicillin-resistant *Staphylococcus aureus* (MRSA), *Staphylococcus epidermidis, Klebsiella* pneumonia including Carbapenem Resistant *Klebsiella* pneumonia, *Enterococcus faecalis, Enterococcus hirae, Acinetobacter baumannii, Pseudomonas aeruginosa, Streptococcus pyogenes, Mycobacterium terrae*, and *Mycobacterium avium*. In addition to pathogens it is understood that viruses, fungi, Mycobacteria, yeast and spores can also be treated by the methods disclosed herein. Additional listings of pathogens, viruses, parasites and fungi suitable for treatment by the coated clay delivery systems and pharmaceutical compositions employing the same are disclosed in U.S. Publication No. US2021/0046186, which is incorporated by reference in its entirety.

Without being limited to a particular mechanism of action, the medicinal clay composition or pharmaceutical composition provides the coated clay at a pH between about 3 to about 5, preferably about 3.5 to about 4, to reduce the alkaline pH of the tissue or organ in need of treatment (i.e., acidify the wound to aid in eliminating bacterial pathogens). It is desired for the medicinal clay to be effective to be applied at pH conditions less than about 5.0. Moreover, the pH of wounds is generally an alkaline environment, therefore the application of acidic compositions beneficially reduces the pH to an environment where the clays are effective. The methods herein buffer the wound environment to promote healing.

The dose regimen will depend on a number of factors that may readily be determined, such as severity of the affected region and responsiveness of the condition to be treated, but will normally be one or more doses per day, with a course of treatment lasting from a single day, to several days, to several months, or until a cure is effected or a diminution of disease state is achieved. In some embodiments, daily or more than one dose per day for at least 4 days, 5 days, 6 days, 7 days, 10 days, 14 days, 21 days, 30 days or greater are provided as a course of treatment. One of ordinary skill may readily determine optimum dosages, dosing methodologies, and repetition rates. In general, it is contemplated that the formulation will be applied as a single treatment. In other embodiments, the formulation will be applied one to four times daily.

Beneficially, the medicinal clay composition or pharmaceutic composition provides an effective anti-pathogenic reduction of microbial populations on the treated surface, such as the tissue or organ of the body treated. The activity can be measured by calculating the log reduction in number of microorganisms. In an embodiment, a 99.99% log reduction of microbial populations on the tissue or organ of the body is achieved after 24 hour contact. In an embodiment, at least a 2 log reduction, at least a 3 log reduction, or preferably at least a 4 log reduction of microbial populations on the tissue or organ of the body is achieved after 24 hour contact.

Anti-pathogenic efficacy of the clay delivery systems can be shown through various quantifiable measurements, including use of time-kill curve study for determining the rate at which antibiotics kill pathogens (in vitro studies) to demonstrate antimicrobial activity in drug development; serum antimicrobial tests (SBTs) using a patient's serum to determine the effectiveness of an antibiotic (or other therapeutic) (in vitro studies); in vivo studies (e.g., with mice) employing the thigh infection model in neutropenic (to eliminate the effect of immune response) mice. Ex vivo studies (e.g., with harvested porcine tissues) may also be employed.

At least the following phases of evaluations of the medicinal clay delivery systems with various actives are to be conducted:

Phase 1 Investigations—Formulation Quality:
1. Formulation analysis to maximize incorporation of clay in the clay compositions and/or other therapeutic compounds;
2. Formulation analysis to assess impact of additional functional ingredients and/or therapeutic ingredients (or other ingredients) on clay activity levels to demonstrate compatibility of ingredient/components with the clay;
3. Release of clay from formulation in aqueous solutions HPLC analysis against standard curves for each clay and/or other therapeutic compound of interest; calculations of efficiency of reactions and final yields; and/or
4. Retention of activity of clays, including: (a) Comparison of anti-pathogenic activity of starting material and following formulation (and release of relevant compounds—i.e., medicinal clays).

Phase 2 Investigations—Effects in Cell Culture Including Potential Cytotoxic Effects:
1. Investigation of formulation components (in aqueous phase) in primary human keratinocytes; Ensure there a no significant keratinolytic effects; explore effects on keratinocyte migration;
2. Investigation of formulation components (in aqueous phase) in primary human fibroblasts (effects on migration and collagen deposition); endothelial cells (ensure angiogenesis—vascular tube formation); and/or
3. Investigation of formulation components (in aqueous phase) in human peripheral blood mononuclear cells; Inflammatory marker release assays (ELISA)—TGF-b, pro-inflammatory interleukin panel.

Phase 3 Investigations—In Vivo/Ex Vivo Wound Healing Experiments and Case/or Clinical Studies:
1. Investigation of best formulations in models of wound healing (e.g., excisional and incisional models in non- and diabetic mice, ex vivo porcine tissue models); and/or
2. Final formulations in clinical case studies.

Methods of Treatment Using a Cation Source

Methods for treatment as described herein for the medicinal clay compositions and pharmaceutical compositions are further application for methods using a cation source. Methods of treatment using a cation source (in place of the medicinal clay and/or pharmaceutical composition) can include a step of applying the cation source and optionally a therapeutic agent, to a subject, namely a tissue or organ in need of treatment. As referred to herein, cation source can include the delivery of a therapeutic agent or can also be a therapeutic cation. The step of applying can include coating a site with a topical application of the cation source. Such topical applications can include for example applying a paste, cream, ointment, foam, hydrocolloid, hydrogel, gel, or the like. The step of applying can also include oral administration, intestinal track, rectal or vaginal administration, such as applying a flowable powder, tablet, capsule, gel, suppository, suspension, dressing or other delivery system.

The methods of treatment are highly effective when a cation source is applied to a tissue or organ in need of treatment and beneficially kills pathogen cells while also being non-cytotoxic, and disrupting, preventing, inhibiting and removing biofilms, secretions, toxins and contaminants from the site (e.g., wound tissue or organ that is infected and in need of treatment). In embodiments, the cation source includes for example, an iron/aluminum complex. A cation source can include cations such as iron (particularly reduced $Fe^+$ and $Fe^{2+}$) aluminum (particularly $Al^{3+}$), and the like. A cation source can additionally include therapeutic agents such as silver ($Ag^+$), and the like.

The methods of treatment can result in a decrease in the alkaline pH of a tissue or organ in need of treatment. In some embodiments, the application reduces the pH of the tissue or organ to less than about 4 to promote healing.

When the cation source comes in contact with a water source (such as a damp wound or wound exudate as a site of treatment), the cations instantly (e.g., within less than about 30 seconds, within less than about 10 seconds, or within less than about 5 seconds) seek to bind with anions, like chloride, in the water source. For example, the water source can be a wound exudate, which contains chloride that can bind and impede efficacy of therapeutic cations, anti-pathogenic cations, or additional cations of the cation source. When the cations of the cation source bind to anions, the action preserves any remaining cations and/or therapeutic agents in the cation source and allows them to retain therapeutic efficacy. Beneficially, cations of a cation source damage pathogen membranes, allowing for the excess cations to cause intracellular protein damage through oxidation. Hydroxyl radicals are generated as $Fe^{2+}/Fe^{3+}/Al^{3+}$ are oxidized by $H_2O_2$ through the Fenton reaction. The proximity of .OH generation to target to be treated (i.e., tissue or organ) is important for toxicity of the pathogen as the radical .OH has a short half-life (estimated at between $10^{-9}$ second half life and also diffuses only nanometers before reacting. In an embodiment, cations, including iron (particularly reduced $Fe^+$ and $Fe^{2+}$) and aluminum (particularly $Al^{3+}$) are provided separate from the medicinal clay.

In some embodiments, the cation source is not activated until it comes into contact with moisture, or a water source, such as upon contacting a tissue or organ of a subject in need of treatment. In embodiments, the methods provide benefits to hospitals and long-term care facilities for only requiring wound care or dressing changes daily. However, in some embodiments where pathogen infections are known to replicate more quickly, more frequent dosing may be preferred. In an exemplary embodiment, when treating MRSA, for example, dosing may be more frequently for an improved kill rate, such as two to four times daily. This will be important to ensure there is a minimum of a 2 log pathogen reduction.

Beneficially, in some embodiments, the cation source also delivers cations into surrounding healthy tissues and further promotes healing. For example, it is envisioned that topical application of cation sources to stomas (i.e., any opening in the skin with exposed mucosal membrane) would benefit from preventative measures to maintain healthy tissues. Such topical application could be in the form of a paste, such as a hydrocolloid paste, to prevent stoma leakage onto surrounding healthy tissue. As a further benefit, in embodiments where a wet stoma is involved cation sources can beneficially dry (through absorbing fluids) and wicks away moisture to keep off the healthy skin.

The methods described herein deliver cations to a subject. Delivery of the cation source may be any one of the delivery applications as described above.

Beneficially the administration of cation sources to a tissue or organ in need of treatment is remineralized by the cation source. Moreover, the cation source provides excess solubilized cations causing intracellular protein damage through oxidation. Exemplary delivery applications can be, but not limited to, topical applications. According to additional embodiments of the disclosure, the cation(s) provided in the cation sources include a minimum effective amount based on about a 1 square inch surface of a subject in need of treatment. In embodiments for topical administration a minimum effective amount of the cation source is between about 0.00001 g and about 10.0 g, between about 0.0001 g and about 8.0 g, between about 0.0005 g and about 6.0 g, between about 0.001 g and about 6.0 g, between about 0.002 g and about 6.0 g, between about 0.005 g and about 6.0 g, or between about 0.05 g and about 6.0 g. In addition, without being limited according to the disclosure, all ranges recited are inclusive of the numbers defining the range and include each integer within the defined range.

According to additional embodiments of the disclosure, the cation(s) provided in the cation sources include a minimum effective amount on a weight basis that is between about 0.001 g and about 2.0 g, or about 0.01 g and about 0.2 g of an aluminum cation source.

According to additional embodiments of the disclosure, the cation(s) provided in the cation sources include a minimum effective amount on a weight basis that is between about 0.003 g and about 4.0 g, or about 0.03 g and about 0.4 g of an iron cation source.

According to additional embodiments of the disclosure, the cation(s) provided in the cation sources include a minimum effective amount on a weight basis that is between about 0.002 g and about 3.0 g, or about 0.02 g and about 0.2 g of a potassium cation source.

According to additional embodiments of the disclosure, the cation(s) provided in the cation sources include a minimum effective amount on a weight basis that is between about 0.001 g and about 2.0 g, or about 0.01 g and about 0.1 g of a sodium cation source.

According to additional embodiments of the disclosure, the cation(s) provided in the cation sources include a minimum effective amount on a weight basis that is between about 0.001 g and about 2.0 g, or about 0.01 g and about 0.1 g of a magnesium cation source.

According to additional embodiments of the disclosure, the cation(s) provided in the cation sources include a minimum effective amount on a weight basis that is between about 0.002 g and about 3.0 g, or about 0.02 g and about 0.2 g of a calcium cation source.

According to additional embodiments of the disclosure, the cation(s) provided in the cation sources include a minimum effective amount on a weight basis that is between about 0.003 g and about 4.0 g, or about 0.03 g and about 0.31 g of a manganese cation source. According to additional embodiments of the disclosure, the cation(s) provided in the cation sources include a minimum effective amount on a weight basis that is between about 0.0005 g and about 8.0 g, or about 0.006 g and about 6.0 g of a silver cation source.

The methods described herein preferably employ cation sources to aid in delivery of therapeutic agents for topical application. The cation sources are preferably applied to the surface of a tissue or organ of the body, such as the skin, mucosal cells and tissues (e.g., alveolar, buccal, lingual, masticatory, or nasal mucosa, and other tissues and cells that line hollow organs or body cavities) or exposed tissue to aid in delivery of therapeutic agents. In an embodiment, the methods described herein preferably employ cation sources for application to skin, mucosal cells, intestinal track, ear canal, nasal passages, oral cavities or combinations thereof to deliver therapeutic agents. The application beneficially prevents the breakdown of skin. Various applications can include use in diapers, underpads for bedding (e.g., for incontinency), hospital drapes, acne, and other applications of skin and wound care.

The cation sources and methods of the present disclosure may be used to deliver therapeutic agents to treat skin that is dry, cracked, itchy, scaly, or exhibiting redness or edema but otherwise appears intact to the unaided eye. Still further the cation sources and methods can be used to deliver therapeutic agents to treat areas in need of pen-wound treatment, such as where nutrients are not otherwise available (e.g., shingles, herpes, hives, poison ivy, and the like), general anti-inflammatory, anti-itch, calming and/or odor control, and the like.

The cation sources and methods may also be used to deliver therapeutic agents to treat more serious wounds, that is, wounds characterized by a partial or total thickness skin loss, including wounds that are at risk of necrosis. When a wound is characterized by a partial or total thickness skin loss, one of the phases of wound healing is the proliferative phase. The proliferative phase typically includes angiogenesis, collagen deposition, granulation tissue formation, epithelialization, and wound contraction. Wound closure thus requires that cells be in a proliferative phase and it is preferred, therefore, that any cation source applied to an open wound to deliver a therapeutic agent not induce the cells in the open wound area into a quiescent state.

In still another embodiment, the methods and the therapeutic agents delivered by cation sources are effective against gastrointestinal pathogens, notably *C. Difficile*.

In various applications of using the cation sources and/or therapeutic agents are delivered for topical applications, in particular for anti-pathogenic treatment and/or prevention. In an embodiment, the cation sources deliver therapeutic agents and thus, provide a vehicle for treating microbial infections, including chronic and non-chronic wounds in need of antimicrobial treatment. In a further embodiment, the therapeutic agents delivered by the cation sources are particularly well suited for treating wounds with an antibiotic resistant pathogen.

In a further embodiment, the therapeutic agents delivered by the cation sources are particularly well suited for treating biofilms commonly found in chronic wound beds and other tissues. In such embodiments, biofilms are found in wound beds, and according to some estimates are present in at least 70% of wound beds. The therapeutic agents delivered by the cation sources disrupt, prevent, inhibit and/or remove biofilms, which means that wound biofilms are treated (including secretions, toxins and contaminants from the site) and further wound biofilm reconstitution is inhibited. Biofilm disruption, or inhibition of biofilm reconstitution, as referred to herein, refers to the ability of the therapeutic agents when delivered to a wound by the cation sources to be able to remove biofilm from a biofilm-containing chronic or acute wound, as well as inhibit reconstitution of biofilm from remnants thereof that may remain after treatment, debridement, or the like. The methods of treating biofilm-containing wounds with the therapeutic agents delivered by cation sources effectively promote healing of such wound which are known to contain multiple different types of bacteria, both Gram positive and Gram negative, within the biofilm that can be difficult to culture as they are clustered within a multicellular matrix-enclosed within the biofilm.

The efficacy according to the methods is effective against a broad range of pathogens, including gram positive and gram negative bacteria. Exemplary pathogens include for example, *Bacillus* spp., *Clostridium* spp. (including *C. Difficile*), *Chlamydia* spp., *Escherichia* spp., *Staphylococcus* spp., *Klebsiella* spp., *Enterococcus* spp., *Acinetobacter* spp., *Pseudomonas* spp., *Streptococcus* spp., *Bordetella* spp., *Borrelia* spp., *Campylobacter* spp., *Brucella* spp., *Mycobacterium* spp., *Salmonella* spp., *Staphylococcus* spp., including for example *Escherichia Coli*, *Staphylococcus aureus*, methicillin-resistant *Staphylococcus aureus* (MRSA), *Staphylococcus epidermidis*, *Klebsiella* pneumonia including Carbapenem Resistant *Klebsiella* pneumonia, *Enterococcus faecalis*, *Enterococcus hirae*, *Acinetobacter baumannii*, *Pseudomonas aeruginosa*, *Streptococcus pyogenes*, *Mycobacterium terrae*, and *Mycobacterium avium*. In addition to pathogens it is understood that viruses, fungi, Mycobacteria, yeast and spores can also be treated by the methods disclosed herein. Additional listings of pathogens, viruses, parasites and fungi suitable for treatment by the coated clay delivery systems and pharmaceutical compositions employing the same are disclosed in U.S. Publication No. US2021/0046186, which is incorporated by reference in its entirety.

The dose regimen will depend on a number of factors that may readily be determined, such as severity of the affected region and responsiveness of the condition to be treated, but will normally be one or more doses per day, with a course of treatment lasting from a single day, to several days, to several months, or until a cure is effected or a diminution of disease state is achieved. In some embodiments, daily or more than one dose per day for at least 4 days, 5 days, 6 days, 7 days, 10 days, 14 days, 21 days, 30 days or greater are provided as a course of treatment. One of ordinary skill may readily determine optimum dosages, dosing methodologies, and repetition rates. In general, it is contemplated that the formulation will be applied as a single treatment. In other embodiments, the formulation will be applied one to four times daily.

Beneficially, the therapeutic agents delivered with the cation sources provide an effective anti-pathogenic reduction of microbial populations on the treated surface, such as the tissue or organ of the body treated. The activity can be measured by calculating the log reduction in number of microorganisms. In an embodiment, a 99.99% log reduction of microbial populations on the tissue or organ of the body is achieved after 24 hour contact. In an embodiment, at least a 2 log reduction, at least a 3 log reduction, or preferably at least a 4 log reduction of microbial populations on the tissue or organ of the body is achieved after 24 hour contact.

Anti-pathogenic efficacy of the therapeutic agents delivered with the cation sources can be shown through various quantifiable measurements, including use of time-kill curve study for determining the rate at which antibiotics kill pathogens (in vitro studies) to demonstrate antimicrobial activity in drug development; serum antimicrobial tests (SBTs) using a patient's serum to determine the effectiveness of an antibiotic (or other therapeutic) (in vitro studies); in vivo studies (e.g., with mice) employing the thigh infection model in neutropenic (to eliminate the effect of immune response) mice. Ex vivo studies (e.g., with harvested porcine tissues) may also be employed.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

The antimicrobial activity of the medicinal clays has been shown to completely eliminate *Escherichia coli, Staphylococcus aureus, Pseudomonas aeruginosa, Salmonella typhimurium*, and antibiotic resistant extended-spectrum beta lactamase (ESBL) *E. coli* and methicillin resistant *S. aureus* (MRSA) within 24 hours in vitro. However, this reported efficacy of medicinal clays, such as rectorite classifications, although widespread is difficult to reproduce. According to some estimates only 50% of rectorites are medicinal or anti-pathogenic. This inconsistency makes it difficult to reproduce as materials labeled as "Rectorite" can have distinct characteristics (including color) and compositions based on where they are mined from and supplied by. Therefore, it can be difficult to reproduce a consistent medicinal clay unless the mineral and other characteristics are sufficiently defined and verified through analysis.

Medicinal clay milled as described according to the product specifications in Table 4 provides an embodiment that provides repeatable and quantifiable medicinal properties.

TABLE 4

| Physical Appearance | |
| --- | --- |
| Color/Appearance | Light tan to gray/green powder |
| Particle Size | <250 micron (desired <50) |
| Activity Indicators | |
| Cation Exchange Capacity (CEC) | >10 mEq/100 g |
| Oxidation-Reduction Potential (ORP) | >250 mV |
| pH | <5.0 |
| Clay Crystalline Composition | |
| Total Combined Illite/Smectite/I-S/Rectorite | >40% |
| Smectite | 10-40% |
| Illite | 10-40% |
| I-S | 20-50% |
| Rectorite [R1, I-S] | 40-50% |
| Active Metallic Ion Content | |
| Aluminum (Al$_2$O$_3$) | 10-30% |
| Elemental | 5-15% |
| Iron (pyrite) | 4-20% |
| Iron (III) Oxide | 0-10% |
| Sulfur | 0-20% |
| Inactivity Measures | |
| Calcite | <0.5% |
| Carbonate | <0.5% |
| Kaolinite | <3.5% |

TABLE 4-continued

| Heavy Metals (limits per FDA guidelines) | |
| --- | --- |
| Heavy Metals (total) | <40 ppm |
| Microbiological Assay (Following Processing/Sterilization Protocol) | |
| Total Plate Count (USP <61>) | <10 cfu/g |
| Yeast/Mold (USP <61>) | <10 cfu/g |

Example 2

Medicinal clay in a pharmaceutical composition was applied to an exemplary wound dressing, which incorporated an additional therapeutic cation, silver. Wound exudate is known to contain anions, which can interfere with the medicinal qualities of the medicinal clay and additional therapeutic agents when the medicinal clay comes into contact with the moisture of the wound exudate (a water source). Wound exudate is variable patient to patient, so an average amount of 101 mEq/L chloride anions was used. The medicinal clay of Example 1 was analyzed for cations, which may interact with the chloride in wound exudate. Table 5 describes an approximate amount of ions present the exemplary clay composition of the wound dressing (4×4 inch pad), silver added into the wound dressing for delivery with the clay, and wound exudate, as well as the amount of each in the exemplary wound dressing and wound exudate (grams). Each of the cations of the clay composition shows an exemplary calculation of the minimum effective amount for a composition that can bind to the chloride to ensure delivery of the silver cation. A skilled artisan will appreciate from the disclosure of the calculations that such a minimum effective amount can vary based on an exudate sample. Accordingly, the calculated atoms and weight (g) in Table 5 can have a variation of about ±30%, ±25%, ±20%, ±15%, or ±10%. The exemplary wound dressings comprise from about 0.1 to about 2.5 grams of the clay composition, preferably from about 0.2 to about 0.8 grams of the clay composition.

TABLE 5

| Source | Ion | Atoms | Weight/Dressing (g) | Atomic Mass | Type |
| --- | --- | --- | --- | --- | --- |
| Exudate | Chloride | 9.70127E+19 | 0.005718 | 35.5 | Anion |
| Clay | Aluminum | 3.5002E+21 | 0.1568 | 26.9815 | Cation |
| Clay | Iron | 2.61433E+20 | 0.02424 | 55.845 | Cation |
| Clay | Potassium | 2.21829E+20 | 0.144 | 39.0983 | Cation |
| Clay | Sodium | 2.43131E+20 | 0.00928 | 22.989 | Cation |
| Clay | Magnesium | 1.8042E+20 | 0.00728 | 24.303 | Cation |
| Clay | Calcium | 9.73827E+19 | 0.00648 | 40.078 | Cation |
| Clay | Manganese | 1.75412E+18 | 0.00016 | 54.938 | Cation |
| In Dressing | Silver | 1.6751E+20 | 0.03 | 107.8682 | Cation |

Table 6 shows the total amount of cations in the exemplary wound dressing (clay+ silver particles) compared to the total amount of anions in the wound exudate and a calculated difference. By subtracting the anions from the total cations, Table 6 shows a net positive amount of cations confirming the ability of the clay composition to completely bind with the chloride and ensure delivery of the silver cations.

TABLE 6

| Clay | Cation Atoms | 4.50615E+21 |
|------|--------------|-------------|
| Exudate | Anion Atoms | 9.70127E+19 |
| Dressing | Silver Particles | 1.34008E+20 |
| | Difference | 4.90914E+21 |

Table 7 shows the calculated percent of each ions (i.e. cation source) in the exemplary wound dressing described above that is needed to bind the total amount of chloride present (101 mEq/L) that the dressing can absorb. One skilled in the art will appreciate from the description herein that one or more cation sources can be provided (instead of the clay compositions described containing multiple cation sources), therefore ranges of ions are shown to accommodate combinational use of each ion as a cation source. The percentage of ions in this exemplary wound dressing can thus also reflect an exemplary amount for different exemplary dressings and different sized dressings as described in the Specification. The remainder of the weight is the clay and dressing material (i.e., pad, gauze, and the like).

TABLE 7

| Ion | % of Dressing |
|-----|---------------|
| Cation Source Aluminum | 0.0016%-1.6% |
| Iron | 0.0032%-3.2% |
| Potassium | 0.0022%-2.2% |
| Sodium | 0.0013%-1.3% |
| Magnesium | 0.0014%-1.4% |
| Calcium | 0.0023%-2.3% |
| Manganese | 0.0032%-3.2% |
| Silver | 0.0062%-6.2% |

Table 8 demonstrates the lattice energy of the exemplary cations when chelated with chloride of exudate. As can be seen, the lattice energy of the cations of the medicinal clay, such as iron and aluminum, have a higher lattice energy and bind more strongly to the chloride than silver.

TABLE 8

| Cation | Anion | Ion Pair | Lattice Energy (kJ/mol) |
|--------|-------|----------|-------------------------|
| Iron 3+ | Chloride | $FeCl_3$ | 5364 |
| Aluminum | Chloride | $AlCl_3$ | 5137 |
| Iron 2+ | Chloride | $FeCl_2$ | 2569 |
| Manganese | Chloride | $MnCl_2$ | 2510 |
| Magnesium | Chloride | $MgCl_2$ | 2477 |
| Calcium | Chloride | $CaCl_2$ | 2268 |
| Silver | Chloride | $AgCl$ | 783 |
| Sodium | Chloride | $NaCl$ | 769 |
| Potassium | Chloride | $KCl$ | 701 |

Using the average chloride amount of 101 meq/L and using chloride as the only anion, the medicinal clay could bind the chloride from 1.9 Liters of exudate, before the silver and chloride would bind. Without the chelation of chloride provided by the medicinal clay, the chloride could bind 72% of the silver that is in the dressing prior to release.

Tables 5 and 6 demonstrate that when chloride is the only anion in wound exudate, there would still be approximately 4.90914 E+21 cation atoms remaining after the clay has bound the chloride in the wound exudate through contact with the dressing. Because the clay has bound the chloride, the remaining silver in the dressing would have minimal binding to the chloride and be preserved and available for antimicrobial functions.

Example 3

Testing was conducted to confirm the binding of cations in medicinal clay to chlorine in solution. The testing summarized herein confirms medicinal clay as described in Table 4 successfully binds to chlorine in a solution. Sterile water with 0.6% chlorine was purchased from Carolina Chemical, Lot number 22126-1. 9 grams, or 30% w/w, of medicinal clay was used. At ambient temperature the sterile chorine water and the medicinal clay were combined under agitation with a standard paddle mixer blade. The solution was mixed for 24 hours at ambient temperature at 3000 rpms. The sterile chlorine water was separated from the medicinal clay and filtered with a 0.45-micron syringe filter. Chloride anions were extracted by dissolving the medicinal clay in water by an ion chromatography instrument system (MQLTM-0939).

Results showed that there was 0.07% of chloride in the medicinal clay and that there was >10 ppm of chlorine. Thus, the medicinal clay converted substantially all of the chlorine to anionic chloride.

Example 4

Laboratory analysis of medicinal clay compositions' antimicrobial effectiveness was evaluated. Organisms were prepared by inoculating the surface of a Soybean-Casin Digest Agar (TSA) incubated at approximately 32.5° C. for 3 days. Following the incubation period, the plates were washed with sterile Serological Saline Solution to harvest the microorganisms used and dilutions with saline were made, plated on TSA in duplicate, and incubated at approximately 36° C. for 42 hours to determine the concentration. The inoculum level was then adjusted to $10^8$ cfu/mL for use as a stock suspension. Stock suspensions were well mixed and homogenized at inoculation for each organism.

Using saline, positive controls were performed by pour plating to enumerate inoculum levels and verify culture purity during testing and negative controls are performed to establish sterility of media, reagents, and materials used at initiation. Neutralizer suitability using Dey-Engley Neutralizing Broth (DEB) is performed concurrently with kill time testing to confirm the recovery of <100 CFU of the test organism in the subculture media in the presence of product.

A 90% clay/10% hydrogel mixture (18 grams of clay and 2 grams of hydrogel) was prepared and dispensed into a 100 mL sterile flask for each treated specimen, and 0.1 mL of inoculum was added to each container to achieve a final concentration of $10^6$ cfu/mL into the product. The mixture is sampled at 0, 12, 24, and 48 hours while the flask is mixed on a shaker at 120 strokes/minute during the duration of testing.

Serial dilutions from each container were made at the testing intervals using 1 mL of the inoculated test product into 9 mL DEB from 1:10 to 1:1000. Subsequently, 1 mL from each dilution was pour plated on TSA incubated at approximately 36° C. for 48 to 72 hours. After the incubation period, all the plates were counted to determine the number of microorganisms, results were averaged and reported as $log_{10}$ reductions.

Figure 6A:
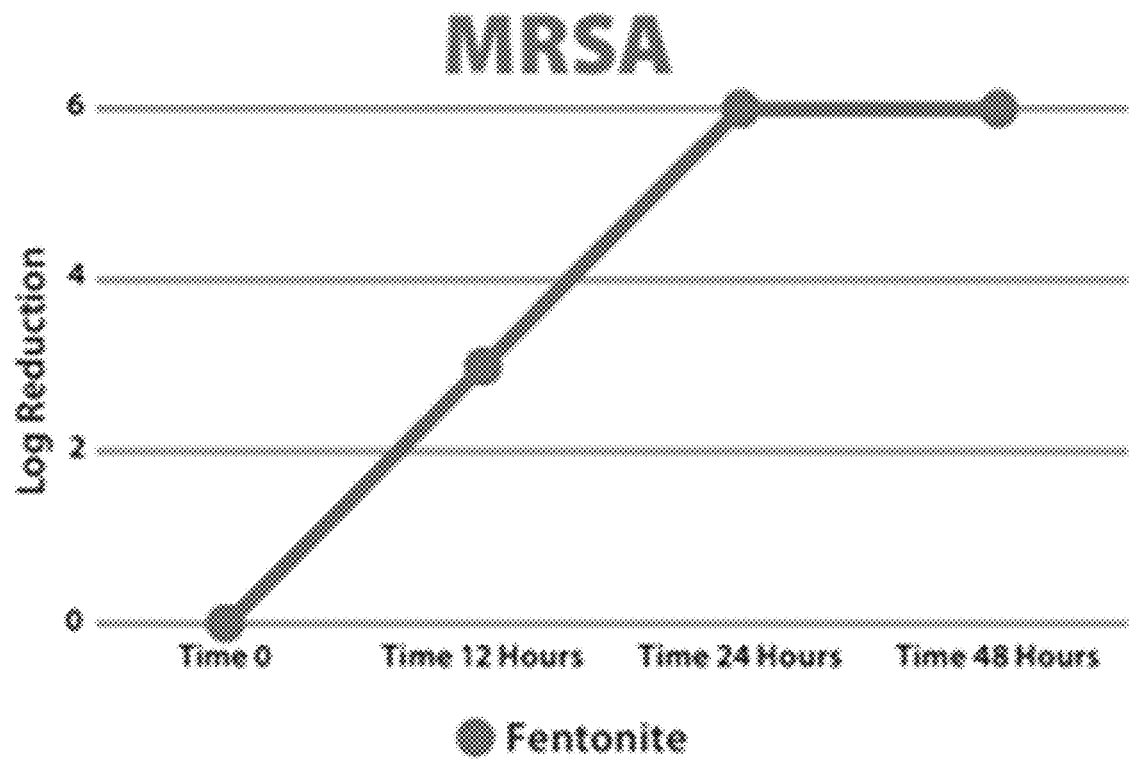
FIGS. 6A-6I show antimicrobial efficacy of medicinal clay compositions as described herein, including log reduction over time against MRSA (FIG. 6A); *Staphylococcus aureus* (FIG. 6B); *Escherichia coli* (FIG. 6C); *Candida albicans* (FIG. 6D); *Pseudomonas aeruginosa* (FIG. 6E); HSV-1 (FIG. 6F); *Streptococcus* pyrogens (FIG. 6G); *Klebsiella pneumoniae* (FIG. 6H); and Clostridioides *difficile* (FIG. 6I).

FIGS. 6A-6I show results of administering the medicinal clay composition as described in Table 4 having the product specifications outlined therein, and evaluated over 48 hours. The results are summarized as follows and depicted in the Figures:

FIG. 6A shows the medicinal clay compositions achieved in excess of a 2 log reduction of MRSA at 12 hours and a 6 log reduction at 24 hours.

Figure 6B:
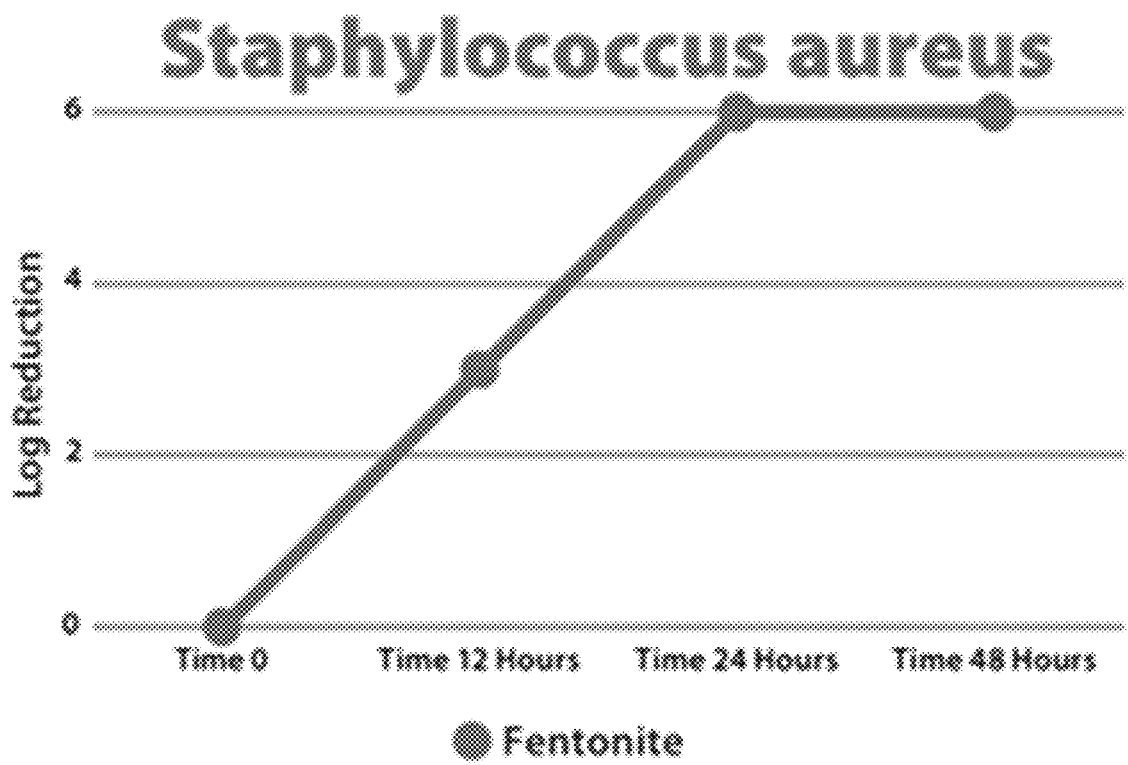

FIG. 6B shows the medicinal clay compositions achieved in excess of a 2 log reduction of *Staphylococcus aureus* at 12 hours and a 6 log reduction at 24 hours.

Figure 6C:
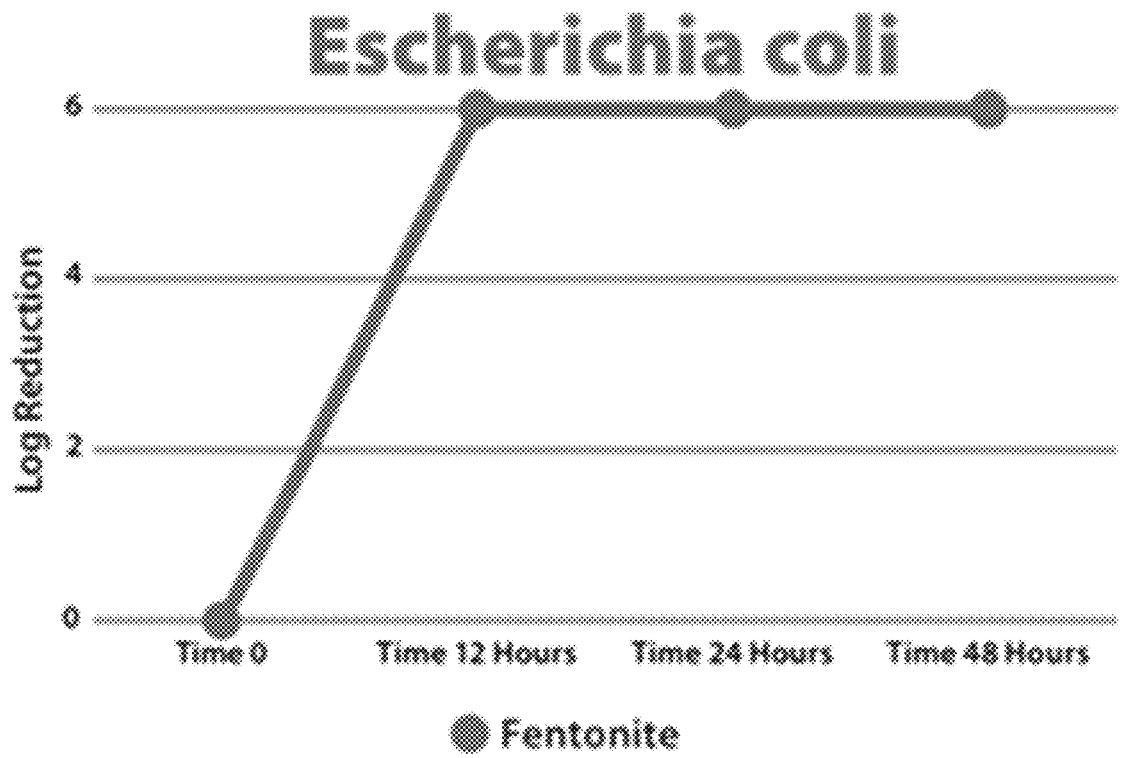

FIG. 6C shows the medicinal clay compositions achieved a 6 log reduction of *Escherichia coli* at 12 hours.

Figure 6D:
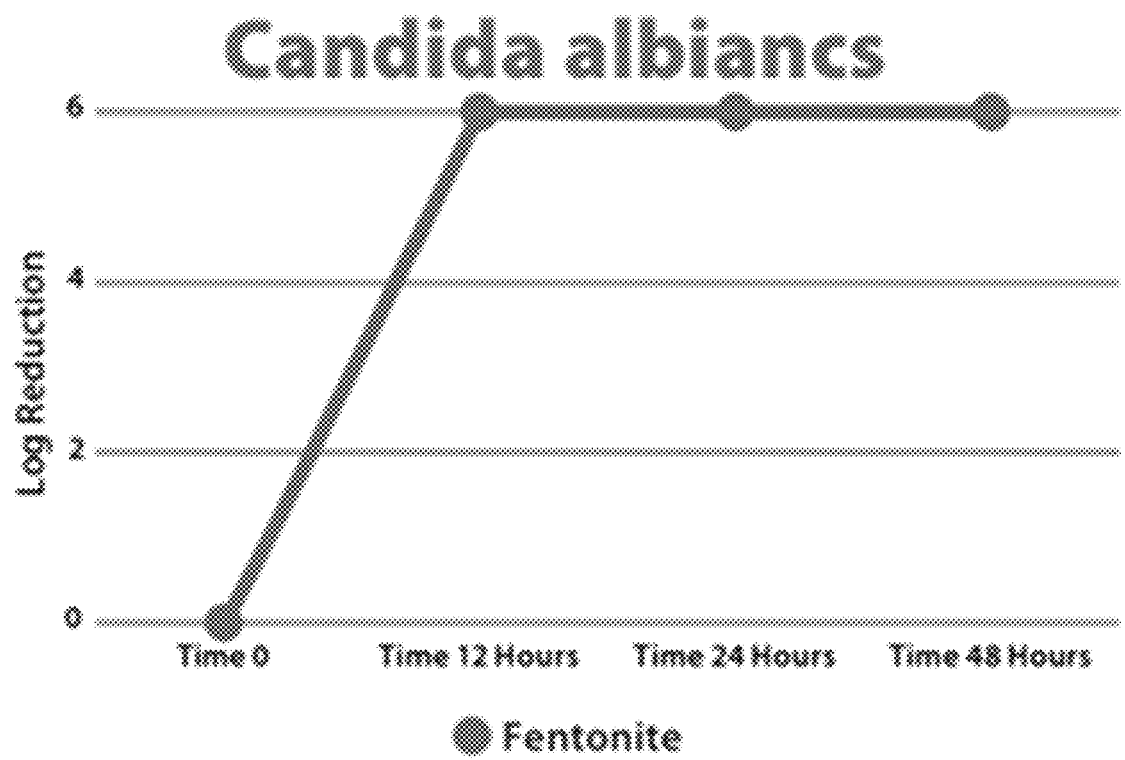

FIG. 6D shows the medicinal clay compositions achieved a 6 log reduction of *Candida albicans* at 12 hours.

Figure 6E:
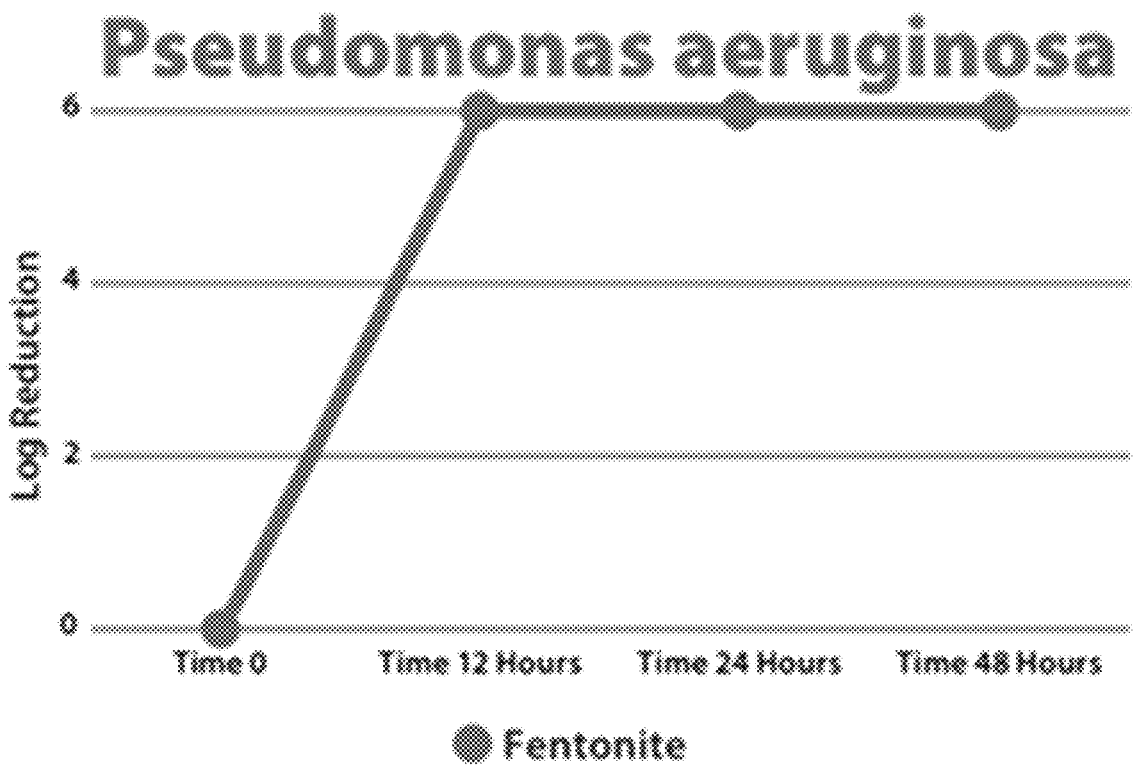

FIG. 6E shows the medicinal clay compositions achieved a 6 log reduction of *Pseudomonas aeruginosa* at 12 hours.

Figure 6F:
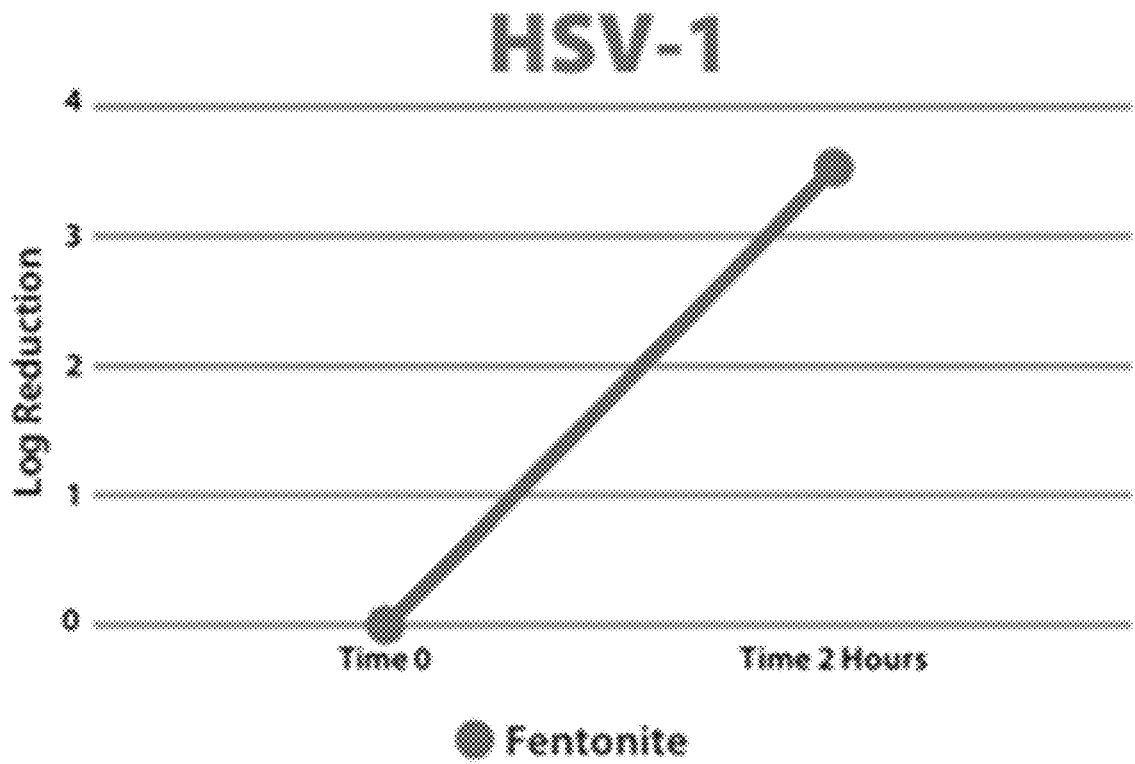

FIG. 6F shows the medicinal clay compositions achieved in excess of a 3 log reduction of HSV-1 at 2 hours.

Figure 6G:
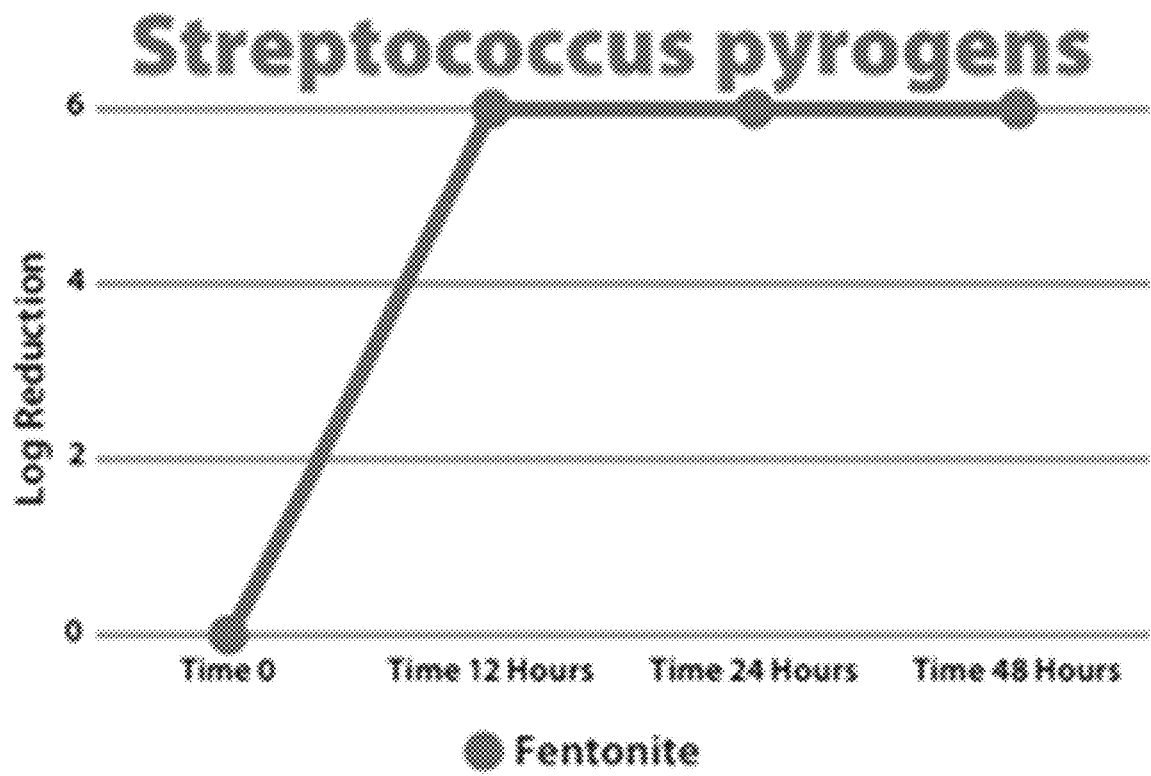

FIG. 6G shows the medicinal clay compositions achieved a 6 log reduction of *Streptococcus* pyrogens at 12 hours.

Figure 6H:
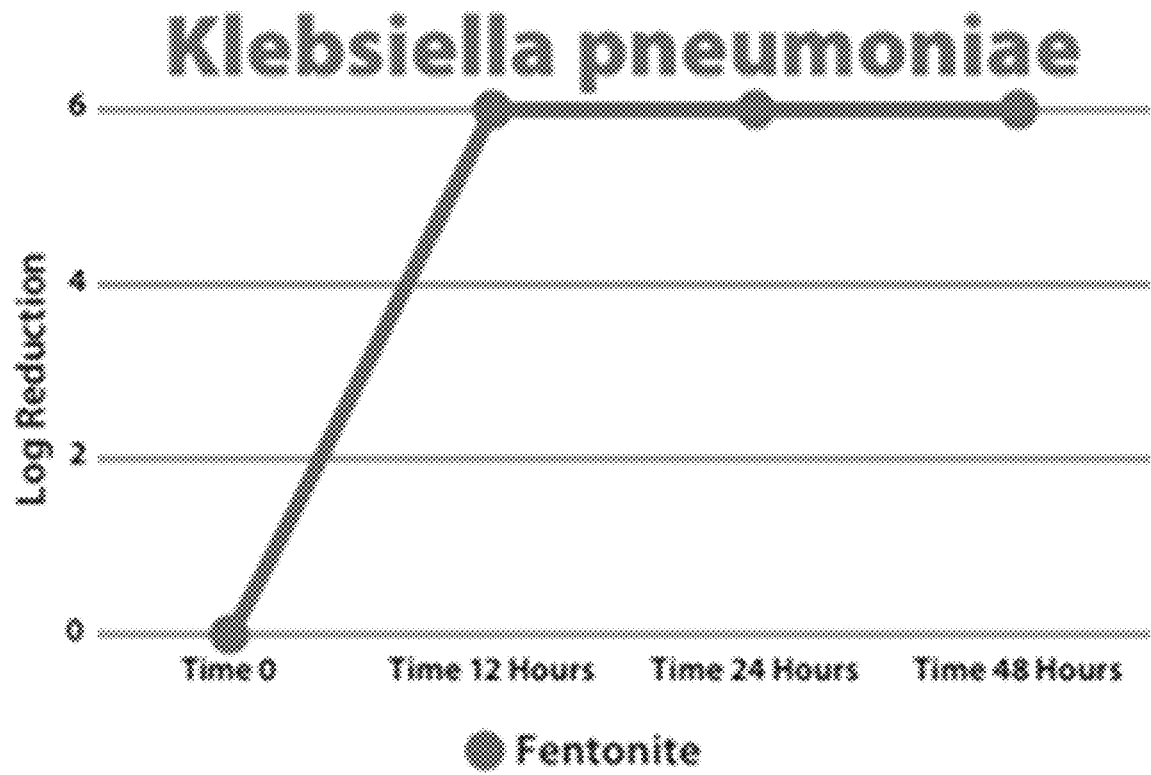

FIG. 6H shows the medicinal clay compositions achieved a 6 log reduction of *Klebsiella pneumoniae* at 12 hours.

Figure 6I:
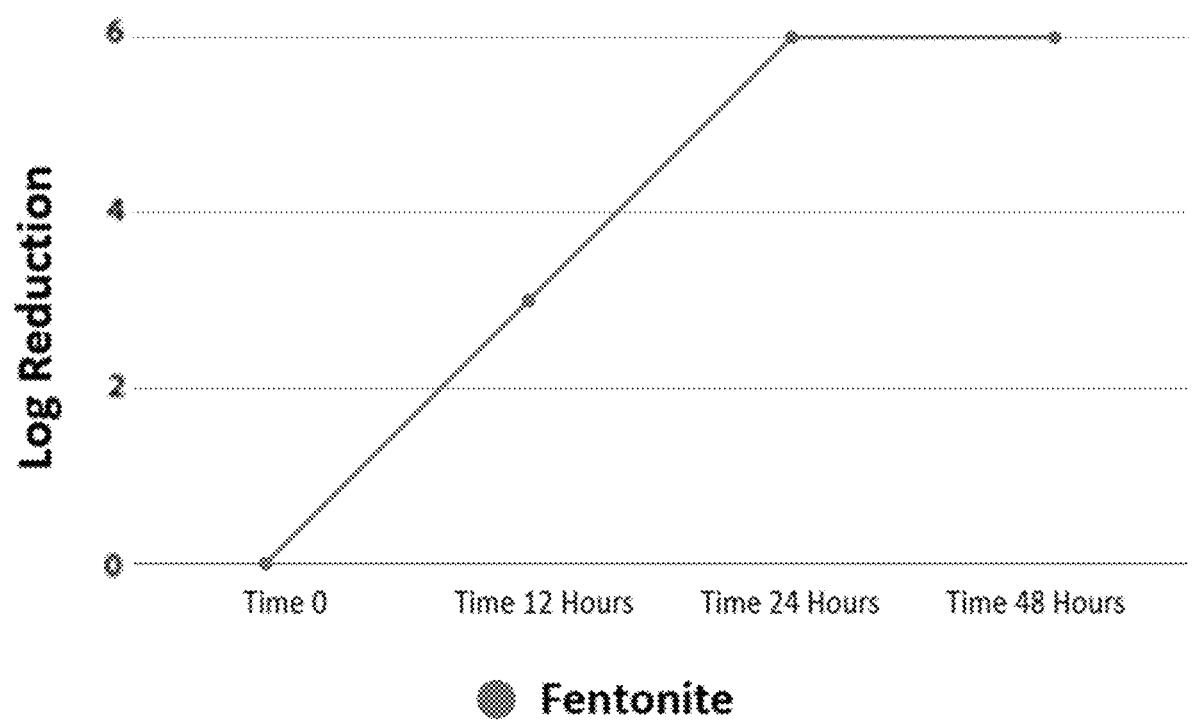

FIG. 6I shows the medicinal clay compositions achieved nearly a 6 log reduction of Clostridioides *difficile* at 24 hours.

Example 5

Additional comparative testing was conducted to show laboratory analysis of antimicrobial efficacy of medicinal clay compositions compared to a competitive product. The medicinal clay and competitive product were prepared and analyzed in the same methods as described in Example 4.

Figure 7:
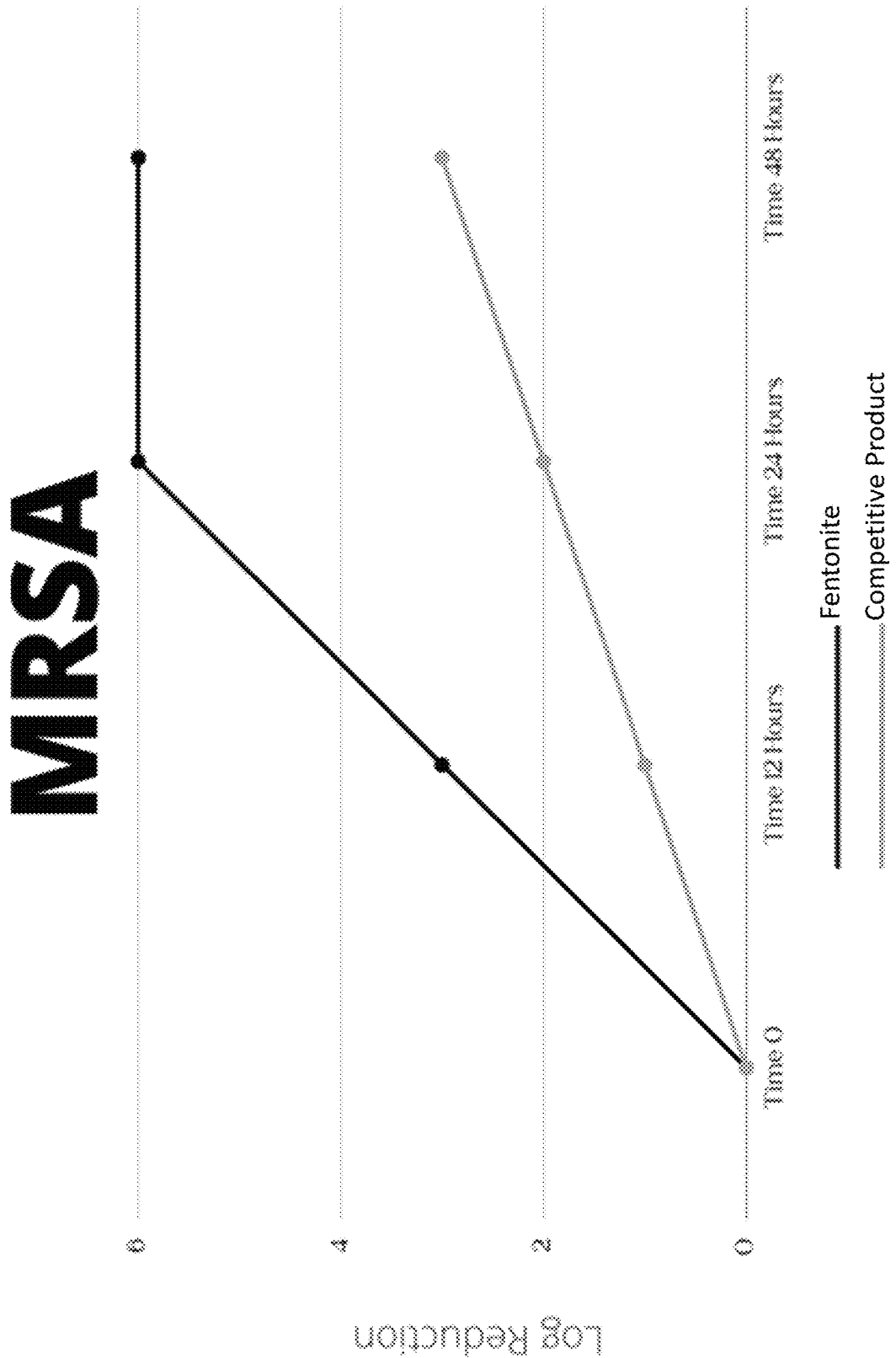
FIG. 7 shows the comparative efficacy of the medicinal clay compositions as described herein to a competitive product, where an embodiment of the invention described provides a 6 log reduction in MRSA at 24 hours compared to competitive product providing a 2 log reduction at the same time point.

FIG. 7 shows the comparative efficacy of the medicinal clay compositions as described herein to a commercially-available Control product (Aquacel Advantage available from Convatec). The results show significant improvement in rate of antimicrobial efficacy of the medicinal clay composition. Notably the medicinal clay composition provides a 6 log reduction in MRSA at 24 hours compared to the commercially-available Control product providing only a 2 log reduction at the same time point. This comparative example showing the improved rate of antimicrobial efficacy shows a significant benefit to the medicinal clay compositions over those of the commercially-available Control product. Additional distinctions and benefits exist. The Aquacel Advantage product, as disclosed in U.S. Pat. No. 9,675,077, use a combination of antimicrobial metal ion (e.g. silver) and a quaternary cationic surfactant (e.g. benzethonium chloride), and also a chelant ethylenediaminetetra-acetic acid (EDTA). The medicinal clay compositions significantly outperform the Control products for a number of reasons. First, the Control product does not account for the deactivation of the antimicrobial metal ion (e.g. silver) in the product as a result of anions, such as chloride, found in wound exudate which bind to and deactivate the silver from having antimicrobial efficacy. Second, the EDTA further acts to bind to and deactivate the antimicrobial metal ion (e.g. silver) in the product. Third, the EDTA also blocks the Fenton reaction from taking place, such that hydroxyl radicals are not generated as the EDTA binds to $Fe^{2+}/Fe^{3+}/Al^{3+}$ instead of allow oxidization through the Fenton reaction. Still further, the Control product includes the cationic antimicrobial—or cationic surfactant as referred to in U.S. Pat. No. 9,675,077, which is a known cytotoxic active and is further known of denature proteins and therefore interfere with the extracellular matrix needed to restore and promote healing at a wound site.

The compositions and methods described herein overcome these shortcomings that are exemplified by the Control product.

Example 6

In vivo testing of an exemplary wound treatment composition was conducted on patient wounds on a human leg to evaluate the antimicrobial and treatment efficacy of the medicinal clay compositions. One patient had 4 different wounds. The exemplary wound dressings were provided as a 2-part suspension wound dressing. The wound dressings were applied and reapplied daily for approximately 9 months. The wound treatment composition was in the form of a cleanser and two-part system as described in Table 9. The hydrogel component of the composition provides an aqueous composition that activates the medicinal clay upon contact with the second part of the composition, providing a coated medicinal clay at the treatment site or wound of the patient.

TABLE 9

| | Wt-% range of component |
|---|---|
| Part 1 - Hydrogel | |
| Poloxamer | 20-50 |
| Glycercin | 2-8 |
| Additional functional ingredients (e.g. preservatives, water) | QS to 100 |
| Part 2 - Suspension | |
| Medicinal Clay | 40-60 |
| Silver | 0.01-0.5 |
| Additional functional ingredients (e.g. xanthan gum, preservatives, glycerin, water) | QS to 100 |

The patient was a 61 year old women with a chronic wound that was previously treated over a period of over 6 years with various medical interventions. Prior treatments included: two split thickness skin grafts that overtime failed; Amniotic Tissue on at least three different occasions; dermal skin used on at least three occasions; and multiple operating room debridements. The patent experienced intermittent improvement with the prior four treatments mentioned. However, overtime during the care the wounds increased in size. The patient was then treated with McCord Health's anti-biofilm cleanser and the above-described wound treatment composition.

The wounds were cleaned and dressing changed 3 times per week. After four months of treatment, two wounds completely resolved. In addition, two wounds reduced 50% in size and healthy viable tissue was visible over the entire area of each wound. The cost of treatment with the wound dressings was a fraction of the cost of prior treatments and the patient is continuing with treatment until full resolution of remaining wounds. These results are further depicted in the figures as described.

Figure 8A:
FIGS. 8A-8H show in vivo studies of the efficacy of the medicinal clay compositions as described herein, where an embodiment described provides treatment of wounds.
Figure 8B:
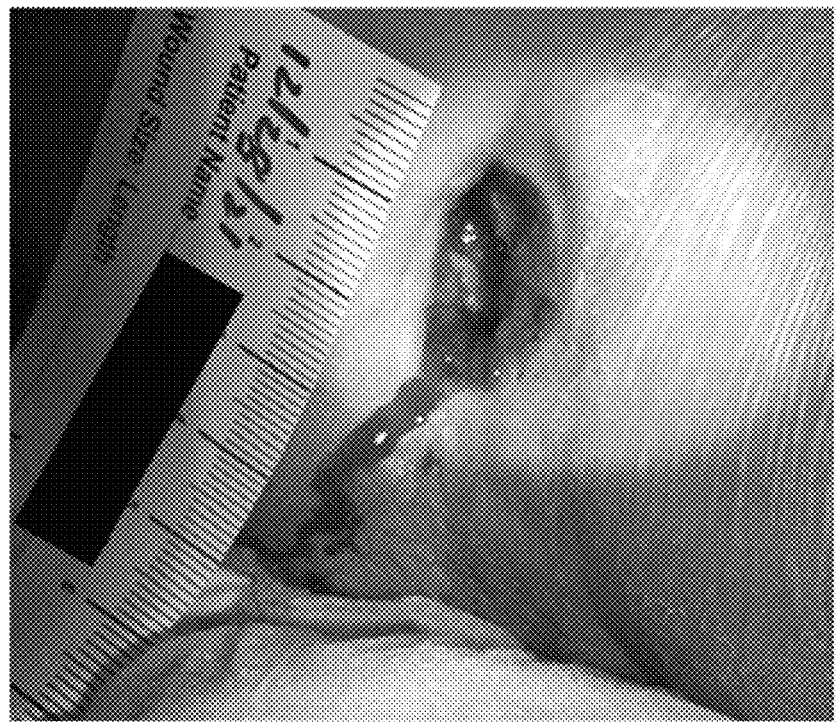
Figure 8C:
Figure 8D:
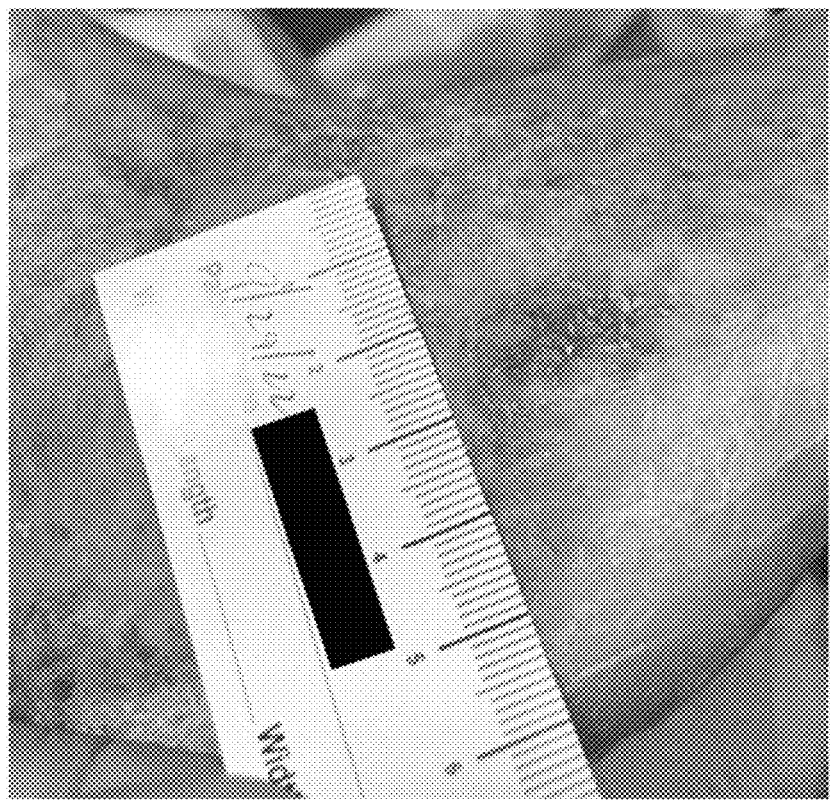

FIGS. 8A and 8B show initial circular wounds of approximately 3-inches on the patient. FIGS. 8C and 8D show the same wounds after 9 months of application of the exemplary pharmaceutical composition (i.e. wound dressing comprising the medicinal clay and silver therapeutic agent) and a decrease in size and depth of the wound.

Figure 8E:
Figure 8F:

FIG. 8E shows an additional wound prior to treatment with the pharmaceutical composition, the initial wound measured approximately 14 inches on the patient. FIG. 8F shows the same wound after 9 months of application of the exemplary wound dressing and a significant decrease in size (approximately 12 inches) and severity of the wound.

Figure 8G:
Figure 8H:

FIG. 8G shows an additional wound prior to treatment with the pharmaceutical composition, the initial circular wound measured approximately 10 inches on the patient. FIG. 8H shows the same wound after 9 months of application of the exemplary wound dressing and another significant decrease in size (approximately 9 inches) and severity of the wound.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. Any reference to accompanying drawings which form a part hereof, are shown, by way of illustration only. It is understood that other embodiments may be utilized and structural changes may be made without departing from the scope of the present disclosure. All publications discussed and/or referenced herein are incorporated herein in their entirety.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A method of treatment of a subject with a composition comprising: administering to a tissue, organ, or wound optionally wherein the tissue, organ, or wound comprises exudate comprising exudate therefrom of a subject in need of treatment a medicinal clay composition and at least one coating agent surrounding the medicinal clay composition, wherein the medicinal clay composition comprises a cation source and has
   a Cation Exchange Capacity of at least about greater than about 10 mEq/100 g,
   an Oxidation-Reduction Potential greater than about 250 mV,
   a pH less than about 5.0, a crystalline composition comprising smectite, illite,
   and/or illite-smectite that is at least about 40 wt-% of the medicinal clay composition,
   and less than 40 ppm heavy metal contaminants,
   and wherein the at least one coating agent comprises a nonionic block Ethylene oxide-propylene oxide (EO-PO) copolymer with an average molecular weight of from about 5,000 to about 20,000,
   wherein said coating agent prevents the premature activation of the medicinal clay composition by surrounding the medicinal clay composition,
   wherein the medicinal clay is activated upon contacting a water source,
   wherein the medicinal clay composition reduces the pH of the tissue or organ to less than about 4 to promote healing, and reducing microbial populations on the subject and/or removing exudate from the tissue, organ, or wound in need of treatment.

2. The method of claim 1, wherein the microbial populations comprise a biofilm.

3. The method of claim 1, wherein the composition is administered to a wound.

4. The method of claim 1, wherein the tissue or organ is skin, mucosal cells, intestinal track, ear canal, nasal passages or oral cavities in need of treatment thereof.

5. The method of claim 1, wherein the method reduces an alkaline pH of tissue, organ, or wound in need of treatment.

6. The method of claim 1, wherein the water source is wound exudate.

7. The method of claim 1, wherein the cation source is selected from the group consisting of $Fe^{2+}$, $Fe^{3+}$, $Al^{3+}$ and combinations thereof to reduce microbial populations by damaging the membranes of the pathogens.

8. The method of claim 7, wherein excess solubilized cations cause intracellular protein damage through oxidation.

9. The method of claim 7, wherein the tissue or organ of a subject in need of treatment is remineralized by the cation source.

10. The method of claim 1, wherein the medicinal clay composition further comprises a therapeutic agent.

11. The method of claim 10, wherein the therapeutic agent is silver and/or silver ions (Ag+).

12. The method of claim 1, wherein the exudate removed from the wound comprises oils, secretions, toxins, and other contaminants.

13. The method of claim 1, wherein the cation source is selected from the group consisting of $Fe^{2+}$, $Fe^{3+}$, $Al^{3+}$ and combinations thereof.

14. The method of claim 11, wherein the cation source chelates chloride anions of the wound exudate maintaining silver cation availability for therapeutic efficacy.

15. The method of claim 13, wherein the cation source is provided to the tissue, organ, or wound at a minimum effective amount based on about a 1 square inch surface of the tissue or organ of the subject in need of treatment in the amount of from about 0.00001 g and about 10.0 g.

16. The method of claim 1, wherein the cation source is administered at least daily or at least weekly to the subject.

17. The method of claim 14, wherein the cation source chelates chloride of the wound exudate maintaining silver cation availability for therapeutic efficacy.

18. The method of claim 1, wherein the at least one coating agent surrounding the medicinal clay composition has a thickness of at least about 5 microns and wherein the average particle size of the clay is less than about 250 microns in diameter.

19. The method of claim 1, wherein the medical clay composition is a crystalline composition comprising a 2:1 tetrahedral/octahedral phyllosilicate with reduced iron octahedral and exchangeable cations, and/or at least 1 wt-% pyrite.

20. A method of treatment of a subject with a composition comprising: administering to a tissue, organ, or wound optionally wherein the tissue, organ, or wound comprises exudate comprising exudate therefrom of a subject in need of treatment a medicinal clay composition and at least one coating agent surrounding the medicinal clay composition, wherein the medicinal clay composition comprises a cation source and has
   a Cation Exchange Capacity of at least about greater than about 10 mEq/100 g,
   an Oxidation-Reduction Potential greater than about 250 mV,
   a pH less than about 5.0,
   a crystalline composition comprising smectite, illite, and/or illite-smectite that is at least about 40 wt-% of the medicinal clay composition,
   and less than 40 ppm heavy metal contaminants, and wherein the at least one coating agent comprises a nonionic block Ethylene oxide-propylene oxide (EO-PO) copolymer with an average molecular weight of from about 5,000 to about 20,000, wherein said coating agent prevents the premature activation of the medicinal clay composition by surrounding the medicinal clay composition, wherein the medicinal clay is activated upon contacting a water source, wherein the medicinal clay composition reduces the pH of the tissue, organ, or wound to less than about 4 to promote healing, and removing biofilm on the subject and/or from the tissue, organ, or wound in need of treatment.

21. The method of claim 20, wherein the medical clay composition is a crystalline composition comprising a 2:1 tetrahedral/octahedral phyllosilicate with reduced iron octahedral and exchangeable cations, and/or at least 1 wt-% pyrite.

* * * * *